United States Patent
Baumann et al.

(10) Patent No.: US 9,971,121 B2
(45) Date of Patent: May 15, 2018

(54) DEVICE FOR SPATIALLY ORIENTING AN X-RAY OPTICAL UNIT AND APPARATUS HAVING SUCH A DEVICE

(71) Applicant: BRUKER NANO GMBH, Berlin (DE)

(72) Inventors: Thomas Baumann, Münster (DE); Ulrich Waldschläger, Berlin (DE)

(73) Assignee: BRUKER NANO GMBH, Berlin (DE)

( * ) Notice: Subject to any disclaimer, the term of this patent is extended or adjusted under 35 U.S.C. 154(b) by 129 days.

(21) Appl. No.: 14/765,712

(22) PCT Filed: Feb. 13, 2014

(86) PCT No.: PCT/EP2014/052852
§ 371 (c)(1),
(2) Date: Aug. 4, 2015

(87) PCT Pub. No.: WO2014/125043
PCT Pub. Date: Aug. 21, 2014

(65) Prior Publication Data
US 2015/0370032 A1    Dec. 24, 2015

(30) Foreign Application Priority Data
Feb. 15, 2013 (DE) .................. 10 2013 202 487

(51) Int. Cl.
*A61B 6/08* (2006.01)
*G02B 7/02* (2006.01)
(Continued)

(52) U.S. Cl.
CPC ....... *G02B 7/023* (2013.01); *G01N 23/20016* (2013.01); *G01N 23/223* (2013.01);
(Continued)

(58) Field of Classification Search
CPC .... G02B 7/02; G02B 7/023; G01N 23/20016; G01N 23/223; G01N 2021/575;
(Continued)

(56) References Cited

U.S. PATENT DOCUMENTS 7,289,597 B2    10/2007  Sasayama et al.
2005/0147347 A1  7/2005  Fluck et al.
(Continued)

FOREIGN PATENT DOCUMENTS

DE    10 2006 011944 A1    10/2006
EP    1 758 132 A1    2/2007
(Continued)

OTHER PUBLICATIONS

International Search Report dated Mar. 26, 2014, mailed Apr. 2, 2014.
(Continued)

*Primary Examiner* — Courtney Thomas
(74) *Attorney, Agent, or Firm* — Norris McLaughlin & Marcus P.A.

(57) ABSTRACT

The invention relates to a device (98) for the spatial alignment of X-ray optics (100) with an entry point (104) and an exit point (108). The device (98) comprises a parallel displacement mechanism (200) for gauging the entry point (104) of the X-ray optics (100) to a first predetermined point (100) by parallel displacement of the X-ray optics (100). Further, the device (98) comprises a goniometer mechanism (300) for gauging the exit point (108) of the X-ray optics (100) to a second predetermined point (106) by at least approximate pivoting of the X-ray optics (100) around the entry point (104). Further, the invention relates to an apparatus (96) which comprises the device (98) and X-ray optics (100).

16 Claims, 9 Drawing Sheets

(51) Int. Cl.
*G01N 23/20* (2018.01)
*G01N 23/223* (2006.01)
*G21K 1/06* (2006.01)
*G01N 21/57* (2006.01)

(52) U.S. Cl.
CPC . *G01N 2021/575* (2013.01); *G01N 2223/076* (2013.01); *G01N 2223/321* (2013.01); *G21K 1/06* (2013.01); *H01J 2235/167* (2013.01)

(58) Field of Classification Search
CPC ....... G01N 2223/321; G01N 2223/076; G21K 1/06; H01J 2235/167
See application file for complete search history.

(56) References Cited

U.S. PATENT DOCUMENTS

| | | | |
|---|---|---|---|
| 2006/0226340 A1 | 10/2006 | Sasayama et al. | |
| 2008/0317211 A1* | 12/2008 | Baumann | G21K 1/06 378/145 |
| 2009/0074147 A1* | 3/2009 | Baumann | G21F 5/02 378/150 |
| 2009/0220054 A1* | 9/2009 | Baumann | G21K 1/06 378/205 |
| 2010/0102248 A1 | 4/2010 | Milas et al. | |
| 2012/0293791 A1 | 11/2012 | Milas et al. | |

FOREIGN PATENT DOCUMENTS

| JP | 2006292567 A | 10/2006 |
|---|---|---|
| JP | 2009505111 A | 2/2009 |

OTHER PUBLICATIONS

English Translation of International Search Report dated Mar. 26, 2014, mailed Apr. 2, 2014.
German Office Action dated Oct. 7, 2013.
S. Xu, et al., "Alignment protocol for effective use of jard x-ray quad collimator for micro-crystallofraphy", Optomechanics 2011: Innovations and solutions, SPIE, vol. 8125, No. 1, pp. 1-8, Sep. 8, 2011, Bellingham, WA, USA.
V.Y. Shovkun, et al., "Stend-70: multifunction arrangement for the x-ray capillary products testing", SPIE, vol. 5943, pp. 1-8, Dec. 6, 2006, Bellingham, WA, USA.

* cited by examiner

DEVICE FOR SPATIALLY ORIENTING AN X-RAY OPTICAL UNIT AND APPARATUS HAVING SUCH A DEVICE

This application is a 371 application of PCT/EP2014/052852 filed Feb. 13, 2014, which claims foreign priority benefit under 35 U.S.C. § 119 of German application 10 2013 202 487.8 filed Feb. 15, 2013.

The invention relates to a device for the spatial alignment of X-ray optics with an optical entry point and an optical exit point. Further the invention relates to an apparatus which comprises the device according to the invention and the X-ray optics.

X-ray optics are according to the prior art gauged within a measuring apparatus on a focal spot of an X-ray tube and aligned in a desired direction. One example of X-ray optics is a polycapillary X-ray lens. Polycapillary X-ray lenses comprise an entry focus and an exit focus. During basic gauging of the measuring apparatus, the entry focus is brought into line with a focal spot on an X-ray tube. The focal spot is created by firing an anode with an electrode beam, wherein X-radiation is created.

Due to the fact that the entry focus is brought into line with the focal spot, the largest share possible of the emitted X-radiation can be used to examine a sample. A sample is examined by positioning the exit focus on the surface of the sample.

The object of the invention is now to create a device in order to be able with a first gauge operation to gauge an optical entry point of X-ray optics to a first predetermined point, e.g. a focal spot on an X-ray tube, and in order to then be able with a second gauge operation to gauge an optical exit point of the X-ray optics to a second predetermined point, e.g. a probe, without influencing the first gauge operation to any significant degree.

This task is resolved by a device and an apparatus with the features described in the independent claims. Further preferred embodiments of the invention arise from the remaining features named in the subclaims.

The device according to the invention for the spatial alignment of X-ray optics with an optical entry point and an optical exit point comprises the following:
- a retaining element for retaining and affixing the X-ray optics, so that these are aligned in the z direction in an initial position, and the entry point is located on at least one pivot axis which is structurally predetermined by the device;
- a parallel displacement mechanism connected to the retaining element for gauging the entry point (104) of the X-ray optics (100) to a first predetermined point (102), comprising:
  - first parallel kinematics designed for the parallel displacement of the X-ray optics essentially in a first parallel displacement direction which differs from the z direction,
  - second parallel kinematics designed for the parallel displacement of the X-ray optics essentially in a second parallel displacement direction which differs from the z direction and the first parallel displacement direction;
- a goniometer mechanism which is connected to the retaining element and the parallel displacement mechanism for gauging the exit point of the X-ray optics to a second predetermined point, wherein the goniometer mechanism is designed to conduct at least approximately a pivoting movement of the X-ray optics around the entry point, comprising:
  - First goniometer kinematics designed to pivot the X-ray optics at least approximately around a first pivot axis, wherein the first pivot axis extends in a direction which differs from the z direction.

Within the scope of the present invention, reference is made to a fixed element, three-dimensional, Cartesian coordinate system comprising a coordinate origin and extending from this, an x axis, a y axis and a z axis. Each individual axis is arranged orthogonally to the two other axes.

In this application, the term "direction", if no more detailed definition is given, is used to describe the fixed element (fixed site) direction, regardless of the sign.

An x direction designates a direction which points in the direction of the positive or negative x axis.

A y direction designates a direction which points in the direction of the positive or negative y axis.

A z direction designates a direction which points in the direction of the positive or negative z axis.

An xy plane is a plane which extends in the x direction and the y direction, i.e. at right-angles to the z direction. The x axis and the y axis can thus run within the xy plane or parallel to it.

An xy direction designates a direction which points in the direction of an extension of the xy plane. Thus an infinite number of xy directions are possible which differ from each other. An xy direction can thus in general comprise an x component and a y component, or also only one x component or only one y component. An xy direction is thus at right angles to the z direction.

X-ray optics are means for influencing a beam projection of X-radiation. The optical entry point is a single-sided point which comprises a defined, i.e. predetermined spatial position with a relationship to the X-ray optics. Typically, the entry point can be at a distance from the X-ray optics, i.e. the X-ray optics can be upstream in relation to the radiation dissemination. In a similar manner, the optical exit point is a single-sided point which comprises a defined, i.e. predetermined spatial position with a relationship to the X-ray optics. Typically, the exit point can be at a distance from the X-ray optics, i.e. the X-ray optics can be upstream in relation to the radiation dissemination.

The entry and exit point can be defined by X-ray optics properties of the X-ray optics. Preferably, the entry point is an entry focus and the exit point is an exit focus. Further, the entry and exit point can also be points which are determined e.g. only partially by the properties of the X-ray optics. This can for example be the case when the entry and exit point are arranged on a lens axis, e.g. a symmetry axis (i.e. a middle axis) of the X-ray optics, but their distances from the X-ray optics are not determined by the X-ray optics themselves. The distances from the X-ray optics can be determined on the basis of further considerations (e.g. influenced by environmental parameters) or at random. In principle, depending on the application, random points on the entry and exit side (with the positioned determined prior to gauging in relation to the X-ray optics) can be selected.

Preferably, the X-ray optics are an X-ray lens. Furthermore, the X-ray lens is preferably a capillary lens, in particular a polycapillary lens. X-ray lenses comprise an entry focus as an optical entry point and an exit focus as an optical exit point. Capillary lenses comprises in their interior at least one capillary, in particular a plurality of capillaries. The capillaries of the capillary lens are typically arranged and formed in such a manner that through them, X-rays which penetrate through by means of total reflection are retained in the entry focus and guided onto the exit focus.

Preferably, the X-ray optics are HOPG optics (Highly Oriented Pyrolytic Graphite) or HAPG optics (Highly Annealed Pyrolytic Graphite). In this case also, the optical entry point is an entry focus, and the optical exit point is an exit focus.

Preferably, the X-ray optics are an elliptical monocapillary. The elliptical monocapillary comprises as an optical entry point a source focal point and as an optical exit point an exit focal point.

Preferably, the X-ray optics are furthermore a cylindrical monocapillary. The optical entry and exit point of the cylindrical monocapillaries are (as already defined above in general terms with reference to the X-ray optics) points on the entry and exit side with a defined spatial position with a relationship to the X-ray optics. Preferably, at least the optical entry point lies on a symmetrical axis of the monocapillaries.

The alignment of the X-ray optics in the z direction in the initial position is primarily understood as meaning that the X-ray optics in the initial position are arranged in such a manner that an axis of the X-ray optics, such as a lens axis, i.e. a connecting line which connects the entry point with the exit point, extends in the z direction. In particular, the exit point of the X-ray optics is displaced in a positive z direction in relation to the entry point.

Equally, the second predetermined point typically comprises a spacer component in the positive z direction in relation to the first predetermined point. The positive z direction here designates the direction which points towards the device starting from the entry point.

Here, the exit position is understood as being a position in the X-ray optics starting from which the X-ray optics are typically gauged. Preferably the initial position is characterised by a central position of a displacement or contortion range which is generally possible.

The retaining element is preferably designed to retain and affix the X-ray optics. This can be achieved using a form-fit and/or force-fit connection. In particular, the retaining element comprises a thread for screwing in the X-ray optics.

The at least one pivot axis designates a conceptual, not a physical pivot axis, which is predetermined by the structural properties of the device, and around which the X-ray optics can at least approximately be pivoted by the goniometer mechanism.

The entry point of the X-ray optics is gauged to a first, predetermined (in particular fixed-site) point, whereby the X-ray optics are displaced in parallel using the parallel displacement mechanism, essentially in a first parallel displacement direction and in a second parallel displacement direction which differs from the first parallel displacement direction. The two parallel displacement directions point in a spatial direction which differs from the z direction. The parallel displacement direction can however also comprise a z component, for example.

The first predetermined point preferably designates a focal spot of an anode on an X-ray tube.

Via the parallel displacement mechanism, alongside the gauging of the entry point of the X-ray optics, a displacement also occurs of the at least one pivot axis to the first predetermined point.

Gauging in the z direction can for example be brought about by a spacer element between the X-ray optics and the retaining element. This is particularly advantageous when the X-ray optics can be connected to the retaining element via a screw connection, i.e. the X-ray optics can be screwed into the retaining element. Gauging in the z direction is usually conducted prior to gauging in the first and second parallel displacement direction.

The parallel displacement in the first parallel displacement direction is enabled by the first parallel kinematics, while the parallel displacement in the second parallel displacement direction is enabled by the second parallel kinematics.

The parallel displacement is essentially conducted in a first or second parallel displacement direction. In the present application, "essentially in a parallel displacement direction" means that the parallel displacement is conducted mainly in the respective parallel displacement direction, although also to a relatively small degree in a further direction, i.e. in a direction at right-angles to the respective parallel displacement direction, for example.

The goniometer mechanism serves to gauge the exit point of the X-ray optics to a second, predetermined (in particular fixed-site) point. This is achieved by the at least approximate pivoting of the X-ray optics around the entry point.

The second predetermined point typically designates a virtual point with certain geometric properties within a measuring apparatus which comprises the device according to the invention. The second predetermined point is in particular located on a measuring plane of the measuring device and comprises a marked, i.e. defined position in relation to other components of the measuring device or to the sample. The second predetermined point typically designates a point of a sample to be examined, in particular a target point on the sample surface.

The exit point of the X-ray optics is gauged to the second predetermined point by using the goniometer kinematics to pivot the X-ray optics at least approximately around a first, structurally predetermined pivot axis. Typically, prior to pivoting the X-ray optics, their entry point is aligned to the first predetermined point using the parallel displacement mechanism. Here, the retaining element affixes the X-ray optics in such a manner that even after parallel displacement, the entry point is essentially located on the pivot axis—the pivot axis is thus also displaced together with the entry point. Essentially, following gauging with the parallel displacement mechanism, the pivot axis thus runs through the entry point and the first predetermined point.

Thus the goniometer mechanism is designed to at least approximately conduct a pivoting movement of the X-ray optics around the entry point in such a manner that the entry point remains at least approximately on the previously gauged (fixed-site) first predetermined point. The entry point thus also remains gauged essentially to the first predetermined point following the pivoting movement around the entry point.

In the present case, "at least approximate pivoting around the pivot axis" can be understood to mean a rotation movement or a combination of a rotation and translation movement. The goniometer kinematics are however designed in such a manner that with the typically very small pivot angles of the X-ray optics conducted, a translation movement that occurs in relation to the respective pivot axis which is fixed-site during the pivoting movement can be ignored.

By means of the device according to the invention gauging of the X-ray optics, in particular 2-point gauging, is made possible. This means that by means of the same device, both the entry point of the X-ray optics can be gauged to a first predetermined point, in particular the focal spot of the anode, and the exit point can also be gauged to a second predetermined point, in particular the target point of the sample surface. This gauging procedure corresponds to gauging with three degrees of freedom.

Preferably the first parallel kinematics of the parallel displacement mechanism are a first parallelogram guide and/or the second parallel kinematics of the parallel displacement mechanism are a second parallelogram guide.

By means of parallelogram guides, a parallel displacement of the X-ray optics can be realised at a relatively low cost and with relatively little space required. Due to the typical kinematics of the parallelogram guide, during the parallel displacement in one of the parallel displacement directions, the X-ray optics also describe a relatively minor parallel displacement in relation to this in a right-angled direction in relation to the respective parallel displacement direction. This parallel displacement in the right-angled direction is however negligible for the typically very small parallel displacements conducted in the parallel displacement directions and the very small angle changes required for that purpose within the parallelogram guide.

The parallel displacement in the parallel displacement directions preferably amounts to maximum +−3 mm, in particular a maximum of +−1 mm. Preferably, a contortion of the connecting elements during the parallel displacement amounts to maximum +−5°, further preferably maximum +−3°, in particular maximum +−2°. The parallel displacement in the direction at right-angles to the parallel displacement amounts to a maximum of 2%, in particular a maximum of 1% of the displacement in the parallel displacement direction.

The parallelogram guides comprise in particular a first and a second counter-element, which are connected to each other by means of a connecting element pair (in particular in a flexible manner). For ideal functioning, the two connecting elements have the same length between the respective two connections to the counter-elements. Equally, the distances on the sides of the two counter-elements between their connections to the connecting elements are equal in length.

In accordance with a parallelogram guide, a first connecting plane, which runs through the flexible connections on the sides of the first counter-element and in the direction of the respective parallel displacement direction, is parallel to a second connecting plane which runs through the flexible connections on the sides of the second counter-element. Additionally, a further plane runs through the ends of a first connecting element which are connected to the counter-elements, whose two intersection lines with the connecting planes are aligned at right-angles to the parallel displacement direction. A further plane which runs through the ends of the second connecting element which are connected to the counter-elements is parallel to the plane of the first connecting element. In the initial position, the planes of the connecting elements are typically arranged at right angles to each other in relation to the two connecting planes. If one regards these four planes from the side, i.e. in such a manner that they appear to be straight lines, the four planes form a parallelogram. With a parallel displacement, the first connecting plane remains constantly parallel to the second connecting plane. Equally, the two planes remain constantly parallel to each other due to the connecting elements, although they change the angle to the two connecting planes. With "classic" joints, the connecting planes run through rotational axes or rotation points of the flexible connections, wherein the rotational axes run along the connecting planes and at right-angles to the parallel displacement directions. The flexible connections can preferably be realised by means of flexure bearings. With flexure bearings, the connecting planes run through the flexure bearings, in particular through those ends of the flexure bearings which point away from the connecting elements.

According to a preferred embodiment of the invention, it is provided that the first parallelogram guide comprises the following for the parallel displacement of the X-ray optics in the first parallel displacement direction:
 a first counter-element,
 a second counter-element, and
 a connecting element pair connecting the two counter-elements,
wherein
 the connecting elements of the connecting element pair are respectively connected to the first counter-element on a first connecting plane via at least one first end, and
 the connecting elements of the connecting element pair are respectively connected via at least one second end to the second counter-element on a second connecting plane which is parallel and at a distance from the first connecting plane, which is arranged on the side of the first connecting plane which faces away from at least one pivot axis, and
 in the first parallel displacement direction the at least one first end of one of the connecting elements comprises a first distance to the at least one first end of the other connecting element, and the at least one second end of one of the connecting elements comprises a second distance to the at least one second end of the other connecting element, wherein the first distance is equal to the second distance,
 on one plane which runs along the first parallel displacement direction and at right-angles to the connecting planes, the respective distances of the respective at least one first end to the respective at least one second end of the connecting elements are equal, and
 the first parallelogram guide is mechanically connected via one of its counter-elements to the retaining element, and thus the parallel displacement of the X-ray optics in the first parallel displacement direction can be realised by means of a relative parallel displacement of the counter-element which is mechanically connected to the retaining element to the other counter-element in the first parallel displacement direction.

According to a preferred embodiment of the invention, it is provided that the first parallelogram guide comprises the following for the parallel displacement of the X-ray optics in the first parallel displacement direction:
 a first counter-element,
 a second counter-element, and
 a connecting element pair connecting the two counter-elements,
wherein
 the connecting elements of the connecting element pair on a first connecting plane which runs along the first parallel displacement direction are respectively connected to the first counter-element via at least one first end, and
 the connecting elements of the connecting element pair are respectively connected via at least one second end to the second counter-element on a second connecting plane which is parallel and at a distance from the first connecting plane, which is arranged on the side of the first connecting plane which faces away from at least one pivot axis, and
 in the first parallel displacement direction the at least one first end of one of the connecting elements comprises a first distance to the at least one first end of the other connecting element, and the at least one second end of one of the connecting elements comprises a second distance to the at least one second end of the other connecting element, wherein the first distance is equal to the second distance, and the first parallelogram guide is mechanically connected via one of its counter-elements to the retaining element, and thus the parallel displacement of the X-ray optics in the first parallel displacement direction can be realised by means of a relative parallel displacement of the counter-element which is mechanically connected to the retaining element to the other counter-element in the first parallel displacement direction.

According to a further preferred embodiment of the invention, it is provided that the second parallelogram guide comprises the following for the parallel displacement of the X-ray optics in the second parallel displacement direction:
  a first counter-element,
  a second counter-element, and
  a connecting element pair connecting the two counter-elements,
wherein
  the connecting elements of the connecting element pair are respectively connected to the first counter-element on a first connecting plane via at least one first end, and
  the connecting elements of the connecting element pair are respectively connected via at least one second end to the second counter-element on a second connecting plane which is parallel and at a distance from the first connecting plane, which is arranged on the side of the first connecting plane which faces away from at least one pivot axis, and
  in the second parallel displacement direction the at least one first end of one of the connecting elements comprises a first distance to the at least one first end of the other connecting element, and the at least one second end of one of the connecting elements comprises a second distance to the at least one second end of the other connecting element, wherein the first distance is equal to the second distance,
  on one plane which runs along the second parallel displacement direction and at right-angles to the connecting planes, the respective distances of the respective at least one first end to the respective at least one second end of the connecting elements are equal, and
  the second parallelogram guide is mechanically connected via one of its counter-elements to the retaining element, and thus the parallel displacement of the X-ray optics in the second parallel displacement direction can be realised by means of a relative parallel displacement of the counter-element which is mechanically connected to the retaining element to the other counter-element in the second parallel displacement direction.

According to a further preferred embodiment of the invention, it is provided that the second parallelogram guide comprises the following for the parallel displacement of the X-ray optics in the second parallel displacement direction:
  a first counter-element,
  a second counter-element, and
  a connecting element pair connecting the two counter-elements,
wherein
  the connecting elements of the connecting element pair on a first connecting plane which runs along the second parallel displacement direction are respectively connected to the first counter-element via at least one first end, and
  the connecting elements of the connecting element pair are respectively connected via at least one second end to the second counter-element on a second connecting plane which is parallel and at a distance from the first connecting plane, which is arranged on the side of the first connecting plane which faces away from at least one pivot axis, and
  in the second parallel displacement direction the at least one first end of one of the connecting elements comprises a first distance to the at least one first end of the other connecting element, and the at least one second end of one of the connecting elements comprises a second distance to the at least one second end of the other connecting element, wherein the first distance is equal to the second distance, and
  the second parallelogram guide is mechanically connected via one of its counter-elements to the retaining element, and thus the parallel displacement of the X-ray optics in the second parallel displacement direction can be realised by means of a relative parallel displacement of the counter-element which is mechanically connected to the retaining element to the other counter-element in the second parallel displacement direction.

One of the counter-elements is thus the part of the parallel kinematics which can be displaced in parallel (to the other counter-element). The retaining element is mechanically connected to the counter-elements which can be displaced in parallel. The connecting elements of the connecting element pair are joints which connect the two counter-elements to each other.

At the ends of the connecting elements, the connecting elements are connected to the counter-elements. This connection is created in such a manner that at least approximately, a contortion of the connecting elements relative to the counter-elements is made possible. The approximate contortion can here comprise a rotatory and a translatory portion. The rotatory portion here comprises a vector which points in the direction parallel to one of the connecting planes and at right-angles to the parallel displacement direction. Here, the vector stands at right angles on a plane in which the rotation is conducted.

A connecting element comprises at least one first end (i.e. one first end or several first ends) and at least one second end (i.e. one second end or several second ends). With several first and/or second ends per connecting element, the first ends and/or second ends are respectively arranged offset from each other in a direction parallel to the connecting planes and at right-angles to the first parallel displacement direction. Thus, the first and second ends of the respective connecting element also lie on one plane.

In an initial position, one plane preferably forms a right angle to the connecting planes via the ends of the respective connecting element.

Preferably, it is provided that:
  the first counter-element of the first parallelogram guide and the first counter-element of the second parallelogram guide, or
  the second counter-element of the first parallelogram guide and the second counter-element of the second parallelogram guide
are immovably connected to each other or designed as a single part.

Thus the two parallelogram guides are connected to each other via their respective first or second counter-element, or the two parallel guides are divided into a first or second counter-element. This results in a space-saving compact, interleaved structure of the two parallelogram guides. Thus, a further elongation of a beam path can be prevented.

The two counter-elements of the parallelogram guides which are not immovably connected to each other or designed as a single part are typically arranged at a distance from each other in a direction at right-angles to the connecting planes, so that a relative movement between them is made possible.

Preferably, the goniometer mechanism comprises second goniometer kinematics, which are designed to pivot the X-ray optics at least approximately around a second pivot axis, wherein the second pivot axis extends in a direction which is different from the z direction and the first pivot axis.

The gauging made possible by means of the device thus corresponds to gauging with four degrees of freedom.

Preferably, the first goniometer kinematics (in particular in the initial position) is a first isosceles, symmetrical trapezoidal guide and/or the second goniometer kinematics (in particular in the initial position) is a second isosceles, symmetrical trapezoidal guide.

By means of trapezoidal guides, an at least approximate pivot movement of the X-ray optics can be realised at a relatively low cost and with relatively little space required. Due to the kinematics of the trapezoidal guide, the X-ray optics also continuously describe a relatively low translatory movement during the pivot movement. In order to keep the translatory movement in both pivot directions as even and as low as possible, the initial position is selected in such a manner that the guide describes an isosceles, symmetrical, trapezoidal form. When the X-ray optics are pivoted, the two parallel sides of the trapezoidal form which are still in the initial position are slightly pivoted towards each other. The trapezoidal guide can thus generally also be described as a rectangular guide with a pair of opposite sides which are equal in length.

The translatory movement during the pivot can in practice be ignored for small pivot angles of the X-ray optics. The pivot angle is preferably maximum +−5°, in particular maximum +−2°. The translation of the entry point in relation to the pivot axis is preferably maximum +−0.2 mm/°, in particular maximum +−0.1 mm/°. Preferably, a contortion of the connecting elements in relation to a stationary counter-element (and starting from the initial position) during the goniometer movement amounts to maximum +−5°, further preferably maximum +−3°, in particular maximum +−2°. The smaller the pivot, the lower the amount of translatory movement between the entry point and the first predetermined point to which the entry point has been gauged by means of the parallel displacement mechanism.

The trapezoidal guides comprise in particular a first and a second counter-element, which are connected to each other by means of a connecting element pair (in particular in a flexible manner). The flexible connections can be realised in particular by means of flexure bearings. For ideal functioning, the two connecting elements have the same length between the respective two connections to the counter-elements. The distance on the sides of the counter-elements, which faces the rotational axis, and between the connections with the connecting elements, is however less than the corresponding distance on the sides of the other counter-element.

According to a trapezoidal guide, a first connecting plane runs parallel to the pivot axis of the guide and through the flexible connections on the sides of the first counter-element. Equally, a second connecting plane runs parallel to the pivot axis of the guide and through the flexible connections on the sides of the second counter-element. The first connecting plane is arranged between the pivot axis and the second connecting plane. Additionally, a further plane runs through the ends of a first connecting element which are connected to the counter-elements, whose two intersection lines with the connecting planes are aligned in the direction of the pivot axis. A further plane runs through the ends of a second connecting element which are connected to the counter-elements, whose two intersection lines with the connecting planes are aligned in the direction of the pivot axis. Along the first connecting plane, a first distance of the two planes through the connecting elements is less than a second distance of the two planes along the second connecting plane. Furthermore, a distance between the flexible connections of the first connecting element with the first counter-element and with the second counter-element along the plane of the connecting element is equal to the corresponding distance to the second connecting element. With "classic" joints, the connecting planes run through rotational axes or rotation points of the flexible connections, wherein the rotational axes run in the direction of the pivot axes. The flexible connections can be realised in particular by means of flexure bearings. With flexure bearings, the connecting planes run through the flexure bearings, in particular through those ends of the flexure bearings which point away from the connecting elements.

In the initial position, the two connecting planes are typically arranged parallel to each other. If one regards the total of four planes from the side, i.e. in such a manner that they appear to be straight lines, the four planes form an isosceles, symmetrical trapezoid.

When a goniometer movement is conducted, the angles change between the two connecting elements and the two counter-elements. As a result, a counter-element conducts the goniometer movement in relation to the other counter-element.

According to a preferred embodiment of the invention, it is provided that the first trapezoidal guide comprises at least the following for the at least approximate pivot movement of the X-ray optics around the first pivot axis:
a first counter-element,
a second counter-element, and
a connecting element pair connecting the two counter-elements,
wherein
the connecting elements of the connecting element pair on a first connecting plane which runs in the direction of the extension of the first pivot axis are respectively connected to the first counter-element via at least one first end, and
the connecting elements of the connecting element pair are arranged on a second connecting plane which runs in the direction of the extension of the first pivot axis and (in the area of the first trapezoidal guide) on the side of the first connecting plane, which faces away from the first pivot axis, and which is at a distance from the first connecting plane, are respectively connected via at least one second end to the second counter-element, and
in a direction running along the first connecting plane and at right-angles to the first pivot axis, the at least one first end of one of the connecting elements comprises a first distance to the at least one first end of the other connecting element, and in a direction running along the second connecting plane and at right-angles to the first pivot axis, the at least one second end of one of the connecting elements comprises a second distance to the at least one second end of the other connecting element, wherein the first distance is less than the second distance, and in directions along the course of one plane which runs at
right-angles to the first pivot axis, the respective dis-
tances of the respective at least one first end to the
respective at least one second end of the connecting
elements are equal, and the first trapezoidal guide is mechanically connected via
one of its counter-elements to the retaining element,
and thus the approximate pivot of the X-ray optics
around the first pivot axis can be realised by pivoting
the counter-element which is mechanically connected
to the retaining element towards the other counter-
element.

According to a further preferred embodiment of the
invention, it is provided that the second trapezoidal guide
comprises at least the following for the at least approximate
pivot movement of the X-ray optics around the second pivot
axis:

a first counter-element,
a second counter-element, and
a connecting element pair connecting the two counter-
elements,
wherein
the connecting elements of the connecting element pair on
a first connecting plane which runs in the direction of
the extension of the second pivot axis are respectively
connected to the first counter-element via at least one
first end, and the connecting elements of the connecting element pair
are arranged on a second connecting plane which runs
in the direction of the extension of the second pivot axis
and (in the area of the second trapezoidal guide) on the
side of the first connecting plane, which faces away
from the second pivot axis, and which is at a distance
from the first connecting plane, are respectively con-
nected via at least one second end to the second
counter-element, and in a direction running along the first connecting plane and
at right-angles to the second pivot axis, the at least one
first end of one of the connecting elements comprises a
first distance to the at least one first end of the other
connecting element, and in a direction running along
the second connecting plane and at right-angles to the
second pivot axis, the at least one second end of one of
the connecting elements comprises a second distance to
the at least one second end of the other connecting
element, wherein the first distance is less than the
second distance, and in directions along the course of one plane which runs at
right-angles to the second pivot axis, the respective
distances of the respective at least one first end to the
respective at least one second end of the connecting
elements are equal, and the second trapezoidal guide is mechanically connected
via one of its counter-elements to the retaining element,
and thus the approximate pivot of the X-ray optics
around the first pivot axis can be realised by pivoting
the counter-element which is mechanically connected
to the retaining element towards the other counter-
element.

The first connecting planes run at a distance from the
respective pivot axis. The description of a direction which
runs "along" a plane can also be read as being a direction
which runs parallel to this plane.

One of the counter-elements is thus the part of the
trapezoidal guide which can conduct the pivot movement
around the respective pivot axis to the other counter-ele-
ment. The retaining element is mechanically connected to
the counter-elements which can be displaced in parallel, and
is in particular integrally connected. The connecting ele-
ments of the connecting element pair are joints which
connect the two counter-elements to each other.

At the ends of the connecting elements, the connecting
elements are connected to the counter-elements. This con-
nection is created in such a manner that at least approxi-
mately, a contortion of the connecting elements relative to
the counter-elements is made possible. The approximate
contortion can here comprise a rotatory and a translatory
portion. The rotatory portion here comprises a vector which
points in the direction parallel to the pivot axis. Here, the
vector stands at right angles on a plane in which the rotation
is conducted.

A connecting element comprises at least one first end (i.e.
one first end or several first ends) and at least one second end
(i.e. one second end or several second ends). With several
first and/or second ends for each connecting element, the
first ends and/or the second ends are in each case arranged
offset from the guide in the direction of the respective pivot
axis. Thus, the first and second ends of the respective
connecting element also lie on one plane. This plane thus
also extends in the direction of the respective pivot axis.

In the initial position, the first and second connecting
elements of the respective trapezoidal guide are typically
arranged in parallel to each other. Thus, the trapezoid
appears to be a symmetrical, isosceles trapezoid.

Preferably, it is provided that:
the first counter-element of the first trapezoidal guide and
the first counter-element of the second trapezoidal
guide, or
the second counter-element of the first trapezoidal guide
and the second counter-element of the second trapezoi-
dal guide
are immovably connected to each other or designed as a
single part.

Thus the two trapezoidal guides are connected to each
other via their respective first or second counter-element, or
the two trapezoidal guides are divided into a first or second
counter-element. This results in a space-saving compact,
interleaved structure of the two parallelogram guides.

The two counter-elements of the trapezoidal guides which
are not immovably connected to each other or designed as a
single part are typically arranged at a distance from each
other in a direction at right-angles to one of the connecting
planes of the counter-elements which are not connected, so
that a relative movement between them is made possible.

Preferably, it is provided that at last two of the guides
respectively comprise one first counter-element and one
second counter-element, which are connected to each other
by means of a connecting element pair of the respective
guide. The connecting element pair can connect the counter-
elements in a movable manner, in particular in a flexible
manner. The flexible connection can be implemented by
means of ("classic") joints or flexure bearings. Further, the
connecting element pair can be relatively flexible compared
to the counter-elements.

Further, it is preferably provided that the first counter-
elements are arranged between the second counter-element
of the respective guide and the first pivot axis. Thus the first
counter-elements are on a side facing the first pivot axis and
the second counter-elements are on a side facing away from
the first pivot axis.

Preferably, it is provided that two of the first counter-
elements or two of the second counter-elements of at the at
least two guides are immovably connected to each other or
designed as a single part. Thus, a coupling of the guides comprising the first or second counter-elements is provided. If more than two guides are to be connected to each other via their counter-elements, first counter-elements and second counter-elements of the guides can also be immovably connected to each other or designed as a single part. For example, the first counter-element of the second parallelogram guide can be immovably connected to or designed as a single part with the first counter-element of the first trapezoidal guide and the second counter-element of the second parallelogram guide can be immovably connected to or designed as a single part with the second counter-element of the first parallelogram guide.

According to one preferred embodiment of the invention, it is provided that at least two of the guides are arranged facing each other in a contorted manner and/or interlocking. The guides can be arranged facing each other in a contorted manner around the lens, in particular around the lens axis. In particular, the guides are interlocked in such a manner that the inner guide is arranged between the connecting elements of the outer guide. This results in a particularly compact design of the device.

Further, it is preferably provided that along a mechanical connecting sequence, starting from the retaining element through to a first or second counter-element provided for affixing the device, the retaining element is connected to (in particular immovably) or designed as a single part with a first or second counter-element, and starting from said element, the first counter-elements belonging to the parallelogram guides and/or trapezoidal guides are connected (in particular immovably) to each other or designed as a single part and/or the second counter-elements are connected (in particular immovably) to each other or designed as a single part.

This means that when the retaining element is connected to or designed as a single part with a first counter-element, for example, the second counter-element of the same kinematics is connected to or designed as a single part with a second counter-element of the next kinematics. The first counter-element of these next kinematics is in turn connected to or designed as a single part with a first counter-element of further kinematics, and so on. This pattern is continued until only one counter-element of a kinematics remains. This counter-element is provided to affix the device.

In a further preferred embodiment, it is provided that
the retaining element is (in particular immovably) connected to the first counter-element of the first trapezoidal guide or is designed as a single part,
the second counter-element of the first trapezoidal guide is (in particular immovably) connected to the second counter-element of the second trapezoidal guide or is designed as a single part,
the second counter-element of the first trapezoidal guide is (in particular immovably) connected to the second counter-element of the second trapezoidal guide or is designed as a single part,
the second counter-element of the first parallelogram guide is (in particular immovably) connected to the second counter-element of the second parallelogram guide or is designed as a single part, and
the first counter-element of the second parallelogram guide is provided to affix the device.

Thus with a parallel displacement conducted initially, the trapezoidal guides are also displaced by means of the parallelogram guides.

Preferably, it is provided that the device further comprises adjusting elements which are designed to introduce a first adjusting force into the first counter-element of the first parallelogram guide, wherein the first adjusting force comprises a component in the first parallel displacement direction (as a result of which the parallel displacement of the X-ray optics can be conducted in the first parallel displacement direction), and
to introduce a second adjusting force into the first counter-element of the first parallelogram guide, wherein the second adjusting force comprises a component in the second parallel displacement direction which can be guided via the connecting elements of the first parallelogram guide to the second counter-element of the first and second parallelogram guide (as a result of which the parallel displacement of the X-ray optics can be conducted in the second parallel displacement direction), and/or
to introduce a third adjusting force into the first counter-element of the first trapezoidal guide, wherein the third adjusting force comprises a component at right-angles to the first pivot axis and parallel to one of the connecting planes of the first trapezoidal guide (as a result of which the approximate pivoting of the X-ray optics can be conducted around the first pivot axis), and
to introduce a fourth adjusting force into the first counter-element of the first trapezoidal guide, wherein the fourth adjusting force comprises a component at right-angles to the second pivot axis and parallel to one of the connecting levels of the second trapezoidal guide, which can be guided via the connecting elements of the first trapezoidal guide onto the second counter-element of the first and the second trapezoidal guide (as a result of which the approximate pivoting of the X-ray optics around the second pivot axis can be conducted).

The components of the third and fourth adjusting force run in particular at right-angles to the first pivot axis and parallel to the connecting plane of the counter-element to be pivoted. In particular, the component of the third adjusting force runs parallel to the first counter-element, and the component of the fourth adjusting force runs parallel to the second counter-element. Preferably, the values of the components essentially correspond to the respective values of the adjusting forces.

Fine-thread mandrels are preferred as adjusting elements. This makes it possible to conduct precise gauging.

Due to the fact that the adjusting elements introduce the respective adjusting force into the respective first counter-element of the parallelogram guides and/or the trapezoidal guides, i.e. into the counter-element between the second counter-element and the pivot axes, the adjusting elements are arranged on the same end section of the mechanics. This makes it possible to gauge online.

The adjusting forces create the parallel displacement or pivoting of the respective counter-element. The adjusting forces can for example be absorbed by means of spring elements which are designed to introduce a spring force into the respective (first) counter-element. The spring forces each comprise a component with an orientation which is the opposite to the component of the adjusting force. Thus, with parallel displacement or pivoting, the spring force is increased or reduced until sufficient parallel displacement or pivoting has been achieved. Through compression or expansion of the spring elements, the spring force is increased or reduced in the known manner until the static balance has been achieved.

As a counter-bearing for the first and second adjusting force and/or as a counter-bearing for the third and fourth adjusting force, a single spring element can preferably be provided. The spring element here acts on the first counter-element and has a spring force with components which are in the opposite direction to the components of the first and second adjusting force and/or the third and fourth adjusting force described above.

Preferably, it is provided that the connecting elements of the connecting element pairs are connected to the first counter-elements and the second counter-elements via ends of the connecting elements. The ends can here have special properties which optimise the connection between the connecting elements and the counter-elements.

Preferably, it is provided that the ends of the connecting elements comprise joints or flexure bearings, in particular one joint or flexure bearing for each end. Thus the connecting elements are connected to the first and second counter-element by means of the joints or flexure bearings. Flexure bearings have the advantage of play-free guidance, and furthermore, no breakaway torque needs to be overcome when actuating the joints. In particular, as a result of the flexure bearings, a reduction in the number of parts is made possible compared to "classic" kinematics. The flexure bearings are in particular arranged between the two connecting planes and are preferably limited by the connecting planes on their sides facing away from the connecting elements.

The flexure bearings are in particular flat bodies, the main surfaces of which (the surfaces with the largest surface content) preferably point in the direction of the parallel displacement direction (both signs) with a parallel guide. With a trapezoidal guide, the main surfaces preferably essentially point in a direction which extends along the respective connecting plane and at right-angles to the pivot axis. In other words, the flexure bearings with their main expansions extend along planes which run at right-angles to the respective connecting plane and at right-angles to the respective parallel displacement direction or in the direction of the respective pivot axis. Thus a flexibility of the flexure bearings in the direction of the parallel displacement direction or in a direction at right-angles to the pivot axis is lower along the respective connecting plane than it is in other directions. Thus, targeted flexure is enabled in the desired direction with a relatively low degree of force.

In order for the two connecting planes of a parallelogram guide to remain parallel even after a parallel displacement, or for the trapezoidal guide to retain the same characteristics after pivoting in both directions, a defined dimensioning of the flexure bearings is required. One criterion can be applied that on one plane which runs in the direction of the parallel displacement direction and at right-angles to the displacement planes, with the parallel displacement the distance between the at least one first end and the at least one second end of a connecting element remains equal to a distance between the at least one first end and the at least one second end of the other connecting element. For this purpose, the flexure bearings of a connecting element have in particular the same deflection curve during parallel displacement as the flexure bearings of the other connecting element. In order to ensure this, identical flexure bearings can be used and the connecting elements can comprise the same longitudinal extensions between the flexure bearings. The connecting elements are preferably essentially rigid in relation to the flexure bearings, although alternatively they can also themselves be designed as flexure bearings between the ends.

With "standard" joints, for example, there is the option of coupling the counter-elements to the connecting elements using pivot joints or ball joints.

Preferably, the two parallel displacement directions are arranged at right-angles to each other. As a result, simple gauging of the entry point of the X-ray optics to the first predetermined point is guaranteed.

Preferably, it is provided that:
the first parallel displacement direction runs in the direction of an extension of an xy plane, and/or
the second parallel displacement direction runs in the direction of an extension of the xy plane and in particular, the second parallel displacement direction forms a right-angle to the first parallel displacement direction.

Via a parallel displacement direction which runs on an xy plane, a parallel displacement of the X-ray optics at right-angles to its alignment in the z direction is possible. The first parallel displacement direction can accordingly run in a first xy direction, and the second parallel displacement direction can run in a second xy direction.

Preferably, the first xy direction is orthogonal to the second xy direction. As a result, the X-ray optics can be displaced in parallel by means of the parallel kinematics in two xy directions which are orthogonal to each other.

Preferably, the two parallel pivot axes are arranged at right-angles to each other. As a result, simple gauging of the exit point of the X-ray optics to the second predetermined point is guaranteed.

According to a preferred embodiment of the invention, it is provided that:
the first pivot axis, at least in the initial position, runs in the direction of an extension of an xy plane, and/or
the second pivot axis, at least in the initial position, runs in the direction of an extension of the xy plane and in particular, the second pivot axis forms a right-angle to the first pivot axis.

Thus, the X-ray optics can be pivoted on a z plane. The z plane is a plane which extends at right-angles to the rotational axis which runs on the xy plane. The first pivot axis can accordingly run in a first xy direction, and the second parallel displacement direction can run in a second xy direction, which are in particular orthogonal to one another.

Preferably, it is provided that the parallelogram guides and/or the trapezoidal guides are arranged in relation to each other in such a manner that the X-ray optics can essentially be retained centrally between the two respective connecting elements of the connecting element pairs by the retaining element.

Due to the central arrangement of the X-ray optics between the connecting elements of the connecting element pairs, a compact arrangement is achieved. For this purpose, the parallel displacement mechanism (in particular the parallelogram guides) and the goniometer mechanism (in particular the at least one trapezoidal guide) comprise an opening which penetrates them. The lens can be arranged within the opening.

Preferably, it is provided that the parallel displacement mechanism and the goniometer mechanism are arranged coaxially in relation to one another, wherein in particular, the goniometer mechanism is arranged coaxially in the parallel displacement mechanism.

The mechanisms and thus the guides can in particular essentially be designed as a hollow cylinder form. Further, at least one of the guides can comprise an opening in which at least one of the other guides is arranged.

Preferably, it is further provided that the parallel displacement mechanism and the goniometer mechanism are essentially designed as a hollow cylinder form, and are arranged coaxially in relation to one another, wherein in particular, the goniometer mechanism is arranged coaxially in the parallel displacement mechanism.

In particular, it is provided that the kinematics are arranged coaxially around the axis of the X-ray optics.

This design provides an optimum use of installation space.

According to a preferred embodiment of the invention, it is provided that the parallel displacement mechanism is designed as a single part and/or the goniometer mechanism is designed as a single part.

The single-part designs can be produced e.g. by lathing, milling, drilling and wire cutting. This permits low-cost production, as a result of which a cost advantage of the device compared to standard adjusting units can be achieved.

In order to clarify the dimensions of the device, several preferred measurements will now be given below:

Thus the device has a height of preferably 30 mm to 150 mm, in particular 40 mm to 70 mm in the z direction and/or a diameter of preferably 20 mm to 100 mm, in particular 30 mm to 50 mm essentially at right-angles to the z direction.

In the z direction, the flexure bearings have a height and/or in a direction essentially at right-angles to the z direction a width of preferably 1 mm to 15 mm, in particular 2 mm to 8 mm. In the respective flexure direction, i.e. in an extension essentially at right-angles to their height and their width, the flexure bearings have a thickness of 0.1 mm to 1 mm, in particular 0.2 mm to 0.6 mm.

Further, an apparatus is provided. The apparatus comprises the device according to any one of the preceding claims and X-ray optics, which are retained and affixed in the retaining element in such a manner that the X-ray optics are aligned in the z direction in an initial position, and the optical entry point is essentially located on at least one pivot axis which is structurally predetermined by the device.

As a result, a unit is provided consisting of the device and the X-ray optics.

The invention will be explained below in exemplary embodiments with reference to the related drawings, in which.

Figure 1:
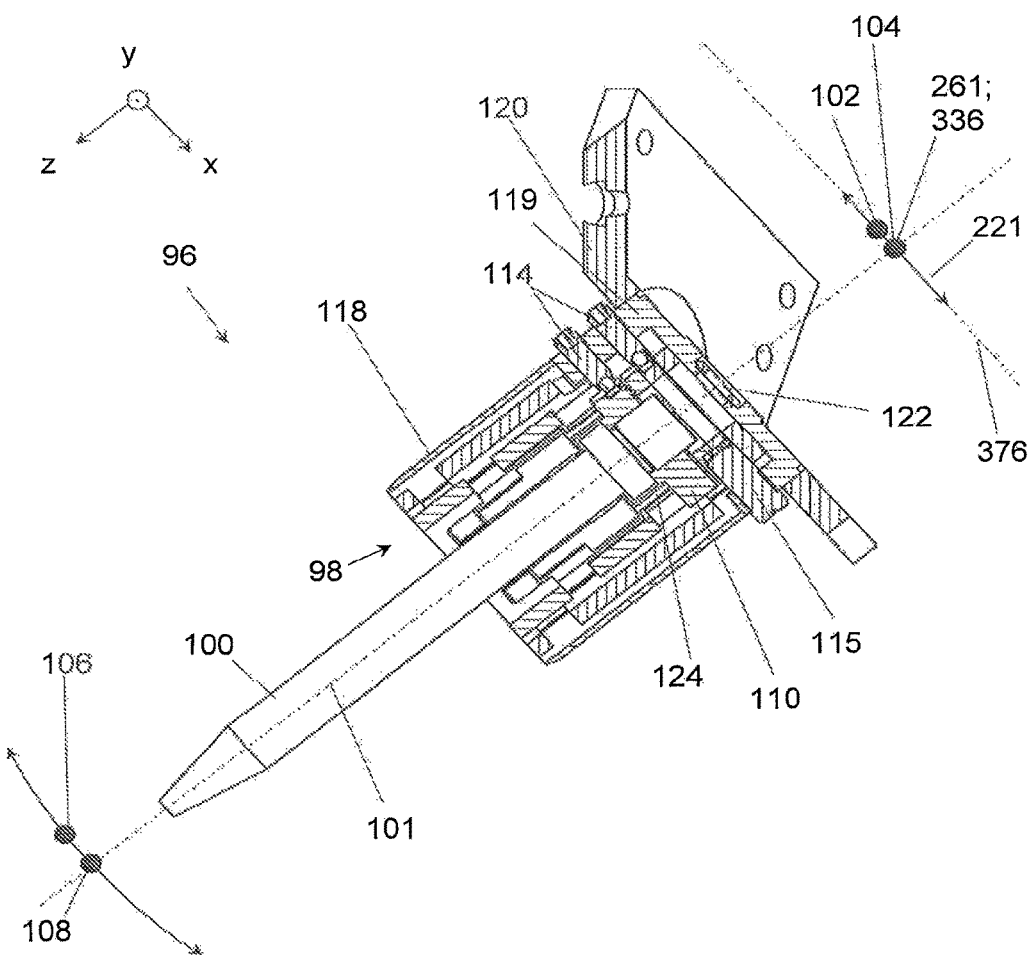
FIG. 1 shows a cross-sectional view of an apparatus.

FIG. 1 shows a cross-sectional view of an apparatus 96 according to a preferred embodiment of the invention with the direction of view counter to the y axis in the negative y direction. A circle with a cross in the centre symbolises an arrow with a view in the arrow direction, while a circle with a point in the centre symbolises a view counter to the arrow direction. The apparatus 96 comprises the device 98 for the spatial alignment of X-ray optics 100, e.g. a capillary lens 100 (i.e. a polycapillary lens), which is arranged in a housing with a first housing part 118, a second housing part 119 and a holder 120 (for affixing the apparatus 96). Further, the apparatus 96 comprises a capillary lens 100 which is not shown in cross-section in a lens housing.

The device 98 and the lens 100 are typically operated in a space with reduced pressure (partial vacuum). The vacuum is typically sealed along an outer sheath wall of the first housing part 118. The holder 120 is here arranged outside the vacuum. The side of the second housing part 119 facing the device is on the sides of the vacuum, while the other side is outside of the vacuum. As a result, adjusting elements 114 (e.g. a fine thread drive) for actuating the device 98 can also be actuated from outside the vacuum. A counter-force to an adjusting force of the adjusting elements 114 can be applied by means of spring elements 115. The adjusting elements 114 and the spring elements 115 can be sealed into the second housing part 119 using grease.

By means of the visible adjusting elements 114, the device 98 can be actuated in such a manner that a parallel displacement in a parallel displacement direction 221 and an at least approximate pivoting of the lens 100 around a first pivot axis 336 (illustrated projected as a dot) can be conducted. By means of two further non-visible adjusting elements, the device 98 can be actuated in such a manner that a parallel displacement in a second parallel displacement direction 261 (illustrated projected as a dot) and an at least approximate pivoting of the lens 100 around a first pivot axis 376 can be conducted.

In the example shown, both the two parallel displacement directions 221, 261 and the two pivot axes 336, 376 run in xy directions, i.e. within an xy plane.

Specifically, as shown, the first parallel displacement direction 221 and the second pivot axis 376 can extend in the x direction and the second parallel displacement direction 261 and the first pivot axis 336 can extend in the y direction. The two parallel displacement directions 221, 261, as well as the two pivot axes 336, 376, can thus form a right-angle in relation to each other.

The lens 100 is in the initial position shown aligned by means of a retaining element 110 in the z direction, and comprises an optical entry point 104 and an optical exit point 108, which are at a distance from each other in the z direction. Since with the X-ray optics 100 shown, this is a capillary lens 100, the optical entry point 104 is an entry focus 104 and the optical exit point 108 is an exit focus 108. Thus, an axis 101 of the X-ray optics 100 is in the case shown a lens axis 101 of the lens aligned in the z direction, and the lens 100 is permeable in the z direction for X-rays. Furthermore, the entry focus 104 of the lens 100 is positioned by means of the retaining element 110 in the intersection of the two pivot axes 336, 376. A window 122 in the second housing part 119 guarantees the least influenced transmission possible of the X-rays and a sealing of the vacuum.

Prior to gauging the entry focus 104 to a first predetermined point 102 (e.g. a focal spot on an anode), it is first checked whether a deviation from the entry focus 104 to the first predetermined point 102 in the z direction is present. Slight deviations can in some cases be offset prior to the remaining gauging using spacer discs of differing thickness (not shown) at the position 124 between the retaining element 110 and the lens 100.

For gauging purposes, the entry focus 104 is first gauged in the parallel displacements 221, 261 to the first predetermined point 102, i.e. it is brought in line with the first predetermined point 102. Here, the pivot axes 336, 376 are also displaced with the entry focus 104, so that the intersection of the pivot axes 336, 376 also concurs with the first predetermined point. Thus, it is guaranteed that with a subsequent pivoting of the lens 100 around the pivot axes 336, 376, the entry focus 104 remains gauged to the first predetermined point 102.

In order to gauge the exit focus 108 to a second predetermined point 106 (e.g. a target point on a sample surface), the lens 100 is approximately pivoted around the pivot axes 336, 376 and thus the entry focus 104. The entry focus 104 remains essentially fixed-site during this goniometer adjustment.

As a result of the gauging process, the entry focus is gauged to the first predetermined point 104 and the exit focus 108 is gauged to the second predetermined point 106. Changes in the distance resulting from the pivoting of the lens 100 in the z direction between the two foci 104, 108 can usually be ignored.

The distances shown between the apparatus 96 and the pivot axes 336, 376, the two foci 104, 108 and the two predetermined points 102, 106 are not shown to scale in the figures.

Figure 2:
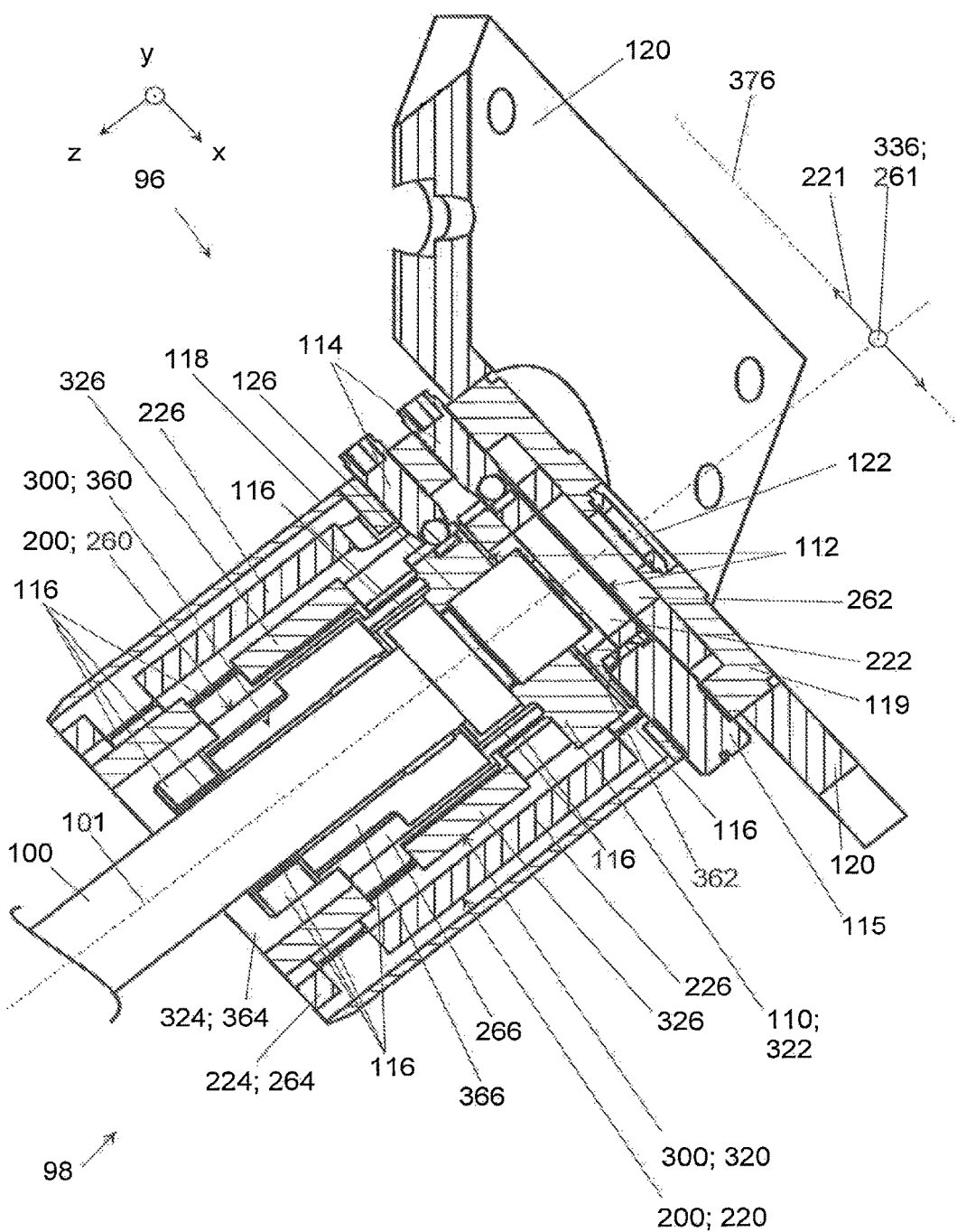
FIG. 2 shows a detailed view of the cross-sectional view of the apparatus.

FIG. 2 shows a detailed view of the cross-sectional view shown in FIG. 1 of the apparatus 96. The device 98 for the spatial alignment of X-ray optics 100 comprises a parallel displacement mechanism 200 and a goniometer mechanism 300.

The parallel displacement mechanism 200 comprises first parallel kinematics 220 for the parallel displacement of the lens 100 in the first parallel displacement direction 221 and second parallel kinematics 260 for the parallel displacement of the lens 100 in the second parallel displacement direction 261. The two kinematics can as shown be designed as a first parallelogram guide 220 and as a second parallelogram guide 260.

The goniometer mechanism 300 comprises first goniometer kinematics 320 for the at least approximate pivoting of the lens 100 around the first pivot axis 336 and second goniometer kinematics 360 for the at least approximate pivoting of the lens around the second pivot axis 376. These two kinematics 320 can be designed as a second symmetrical, trapezoidal guide 360. The description "symmetrical, trapezoidal guide" designates the form of these guides in the initial position shown.

The goniometer mechanism can, as can be seen in FIG. 2, be arranged in particular in the initial position coaxially between the parallel displacement mechanism 200 and the lens axis 101.

The kinematics 220, 260, 320, 360 each comprise a first counter-element 222, 262, 322, 362, which is arranged between the pivot axes 336, 376 and a second counter-element 224, 264, 324, 364.

Specifically, the first parallelogram guide 220 comprises a first counter-element 222 and a second counter-element 224, which are connected to each other by means of two connecting elements 226. The second parallelogram guide 260 comprises a first counter-element 262 and a second counter-element 264, which are connected to each other by means of two connecting elements 266. Of the two connecting elements 266, only one is visible, which in FIG. 2 extends behind the lens 100. As is shown, the two second counter-elements 224, 264, can be integrally connected to each other, i.e. be designed as a joint counter-element. The first counter-element 262 is also used to affix the device in the second housing part 119. This can be achieved by means of screw connections (not shown) for example. There is a gap 112 between the two first counter-elements 222, 262, enabling a relative movement of the first counter-elements 222, 262 to each other.

The first trapezoidal guide 320 comprises a first counter-element 322 and a second counter-element 324, which are connected to each other by means of two connecting elements 326. The second trapezoidal guide 360 comprises a first counter-element 362 and a second counter-element 364, which are connected to each other by means of two connecting elements 366. Of the two connecting elements 366, only one is visible, which in FIG. 2 extends behind the lens 100 and in front of the connecting element 266. As is shown, the two second counter-elements 324, 364, can be integrally connected to each other, i.e. be designed as a joint counter-element. The first counter-element 322 is designed as a single part with the retaining element 110, and thus serves to retain and affix the lens 100. The lens 100 is in the example screwed into the retaining element 110 by means of a screw connection 126. There is a gap 112 between the two first counter-elements 322, 362, enabling a relative movement of the first counter-elements 322, 362 to each other.

The parallel displacement mechanism 200 is connected to the goniometer mechanism 300 via the first counter-element 222 and the first counter-element 362, so that no relative movements in relation to each other are possible. In the example, they are screwed together.

According to the present nomenclature, the respective first counter-element 222, 262, 322, 362 is thus arranged between the pivot axes 336, 376 and the respective second counter-element 224, 264, 324, 364. In other words, the respective second counter-element 224, 264, 324, 364 is at a distance from the respective first counter-element 222, 262, 322, 362 in the positive z direction.

The connections between the connecting elements 226, 266, 326, 366 and the counter-elements 222, 262, 322, 362, 224, 264, 324, 364 are particularly advantageously achieved by means of flexure bearings 116. These will be explained in greater detail in the descriptions of the figures below.

As a result of the use of flexure bearings 116, both the parallel displacement mechanism 200 and the goniometer mechanism 300 can be designed as a single part.

Figure 3:
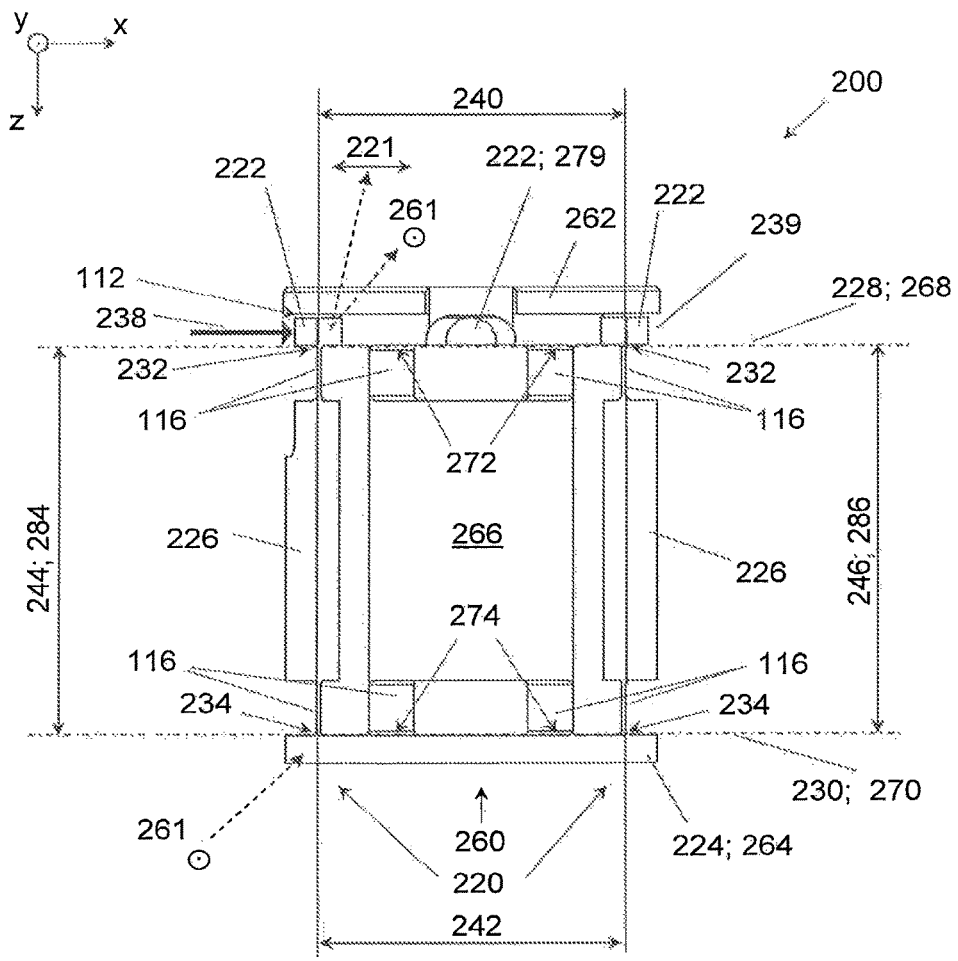
FIG. 3 shows a front view of a parallel displacement mechanism.
Figure 4A:
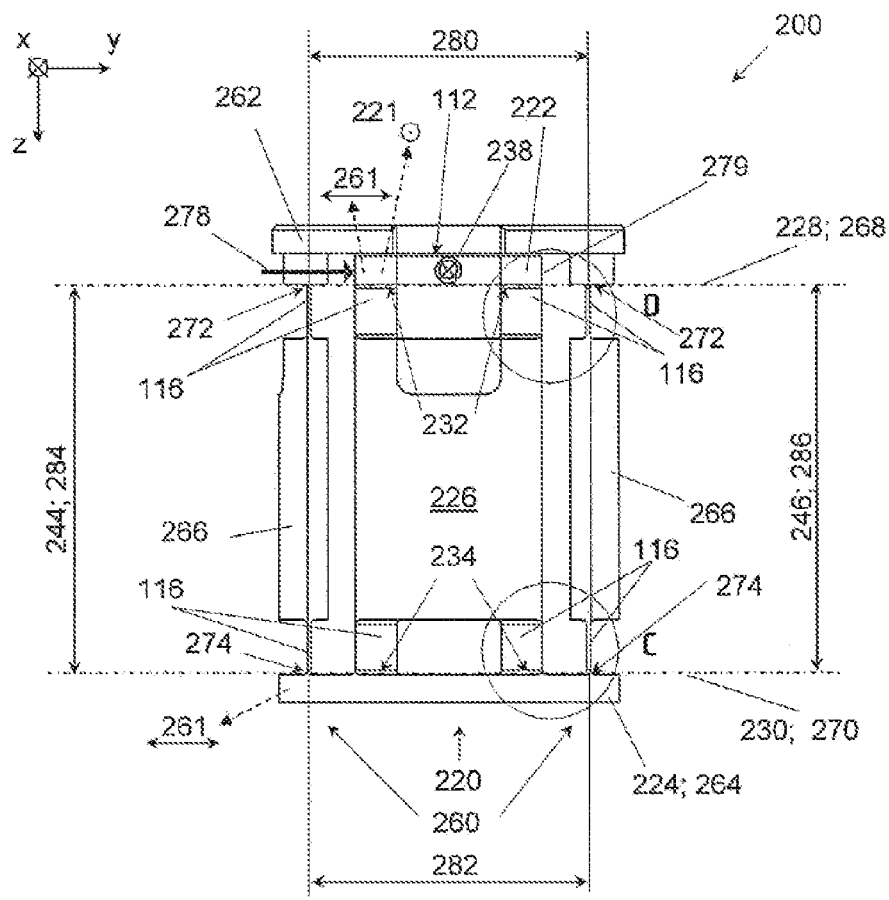
FIGS. 4A-4C show a side view of the parallel displacement mechanism, with FIGS. 4B and 4C showing close up views of sections C and D of FIG. 4A, respectively.
Figures 4B, 4C:
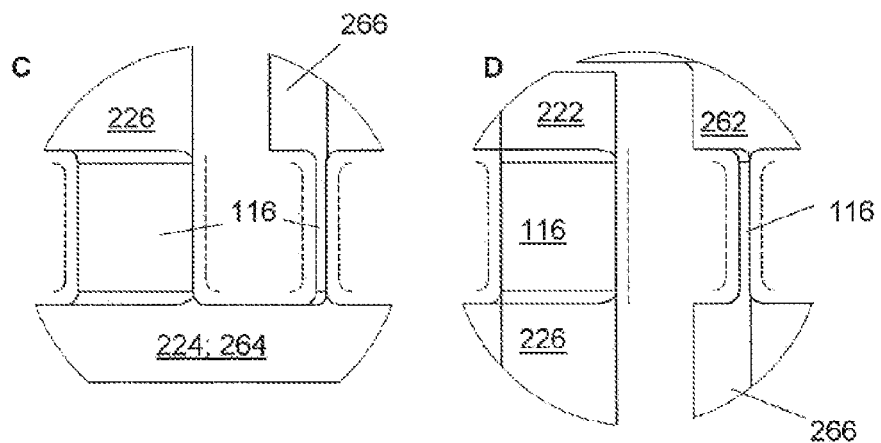

FIG. 3 shows a front view of the parallel displacement mechanism 200, in turn with the direction of view counter to the y axis in the negative y direction. In this view, the first counter-element 222 of the first parallelogram guide 220 is partially covered by the first counter-element 262 of the second parallelogram guide 260, so that the gap 112 (see in particular FIG. 4A) between the first counter-elements 222, 262 is only partially visible. FIG. 4A shows a side view of the parallel displacement mechanism 200 with the view in the direction of the x axis, i.e. in the positive x direction.

The flexure guides 116 connect the connecting elements 226, 266 with the counter-elements 222, 262, 224, 264, wherein the connection is achieved via at least one end 232, 272 (in the example shown, via two ends 232, 272 respectively) and at least one second end 234, 274 (in the example shown, via two ends 234, 274 respectively) of the connecting elements 226, 266. The flexure bearings 116 are dimensioned with respect to their flexure rigidity and flexibility values in such a manner that a force applied to create flexure in the respective parallel displacement direction 221, 261 is considerably lower compared to other spatial directions.

In the first parallelogram guide 220, the connecting elements 226 are connected to the first counter-element 222 on a first connecting plane 228, which runs along the first parallel displacement direction 221, via two first ends 232 in each case. In the example shown, the first connecting plane 228 is an xy plane. On a second connecting plane 230 at a distance from the first connecting plane 228, the connecting elements 226 are in each case connected to the second counter-element 224 via two second ends 234. The second counter-element 224 and the second connecting element 230 are offset from the first counter-element 222 and the first connecting plane 228 in the positive z direction.

In the first parallel displacement direction 221, the two first ends 232 of one of the connecting elements 226 comprise a first distance 240 from the second first ends 232 of the other connecting element 226. In this direction, the two first ends 234 of one of the connecting elements 226 comprise a second distance 242 from the two second ends 234 of the other connecting element 226. The first distance 240 is equal to the second distance 242 in order to achieve a parallelogram guide.

This also results in the fact that on one plane which runs in the direction of the first parallel displacement direction 221 and at right-angles to the two connecting planes 229, 230, the respective distances 244, 246 between the respective first ends 232 and the respective second ends 234 of the connecting elements 226 are equal. The two first ends 232 and the two second ends 234 of the respective connecting element 226 are offset from each other in a direction parallel to the connecting planes 228, 230 and at right-angles to the first parallel displacement direction 221, i.e. in the example, in the y direction.

In order to conduct a parallel displacement of the lens 100 in the first parallel displacement direction 221, a first adjusting force 238 is introduced to the counter-element 222 by means of an adjusting element 114, wherein the first adjusting force 238 comprises a component in the first parallel displacement direction 221. The first adjusting force 238 shown comprises a (sole) component in the positive x direction in the exemplary embodiment. As a result of the adjusting force 238, a flexure of the flexure bearing 116 and thus of necessity a parallel displacement of the first counter-element 222 is thus achieved relative to the second counter-element 224.

The parallel displacement comes to an end when the forces are balanced. This results on the one hand from the first adjusting force 238, which acts in the positive x direction, and on the other hand from forces resulting from the flexure of the flexure bearings 116 as well as a spring force (not shown) which is brought about by a spring element 115 and which acts on a first counter-bearing 239 in the negative x direction. Due to a pre-tensioning of the spring element 115, a parallel displacement can also be conducted in the negative x direction.

In the second parallelogram guide 260, the connecting elements 268 are connected to the first counter-element 262 on a first connecting plane 268, which runs along the first parallel displacement direction 261, via two first ends 272 in each case. In the example shown, the first connecting plane 268 is an xy plane. On a second connecting plane 268 at a distance from the first connecting plane 270, the connecting elements 266 are connected to the second counter-elements 264 via two second ends 274. The second counter-element 264 and the second connecting element 270 are offset from the first counter-element 262 and the first connecting plane 268 in the positive z direction. In the second parallel displacement direction 261, the two first ends 272 of one of the connecting elements 266 comprise a first distance 280 from the second first ends 272 of the other connecting element 266. In this direction, the two first ends 274 of one of the connecting elements 266 comprise a second distance 282 from the two second ends 274 of the other connecting element 266. The first distance 280 is equal to the second distance 282 in order to achieve a parallelogram guide. This also results in the fact that on one plane which runs in the direction of the second parallel displacement direction 261 and at right-angles to the two connecting planes 269, 270, the respective distances 284, 286 between the respective first ends 272 and the respective second ends 274 of the connecting elements 266 are equal. The two first ends 272 and the two second ends 274 of the respective connecting element 266 are offset from each other in a direction parallel to the connecting planes 268, 270 and at right-angles to the second parallel displacement direction 261, i.e. in the example, in the x direction.

In the exemplary embodiment, the first connecting planes 228 and 268 and the second connecting planes 230, 270 of the parallelogram guides 220, 260 are identical.

In order to conduct a parallel displacement of the lens 100 in the second parallel displacement direction 261, a second adjusting force 278 is introduced to the first counter-element 222 of the first parallelogram guide 220 by means of an adjusting element 114, wherein the second adjusting force 278 comprises a component in the second parallel displacement direction 261. The second adjusting force 278 shown comprises a (sole) component in the positive y direction in the exemplary embodiment. The second adjusting force 278 is guided over the rigid flexure bearings 116 of the second parallelogram guide 220 in the second parallel displacement direction 261 to the joint second counter-element 224, 264 of the first and second parallelogram guide 220, 260. Due to the second adjusting force 278, a flexure of the flexure bearings 116 of the second parallelogram guide 260 and thus of necessity a parallel displacement of the second counter-element 264 relative to the second counter-element 264 in the second parallel displacement direction 261 is achieved.

The parallel displacement comes to an end when the forces are balanced in the second parallel displacement direction 261. This results on the one hand from the second adjusting force 278, which acts in the positive y direction, and on the other hand from forces resulting from the flexure of the flexure bearings 116 as well as a spring force (not shown) which is brought about by a spring element 115 and which acts on a first counter-bearing 279 in the negative y direction. Due to a pre-tensioning of the spring element 115, a parallel displacement can also be conducted in the negative y direction.

In the details C and D, the flexure bearings 116 are shown in detail. In some cases, these comprise rounded transitions to the counter-elements 222, 224, 262, 264 and to the connecting elements 226, 266—symbolically shown as broken lines.

Figure 5:
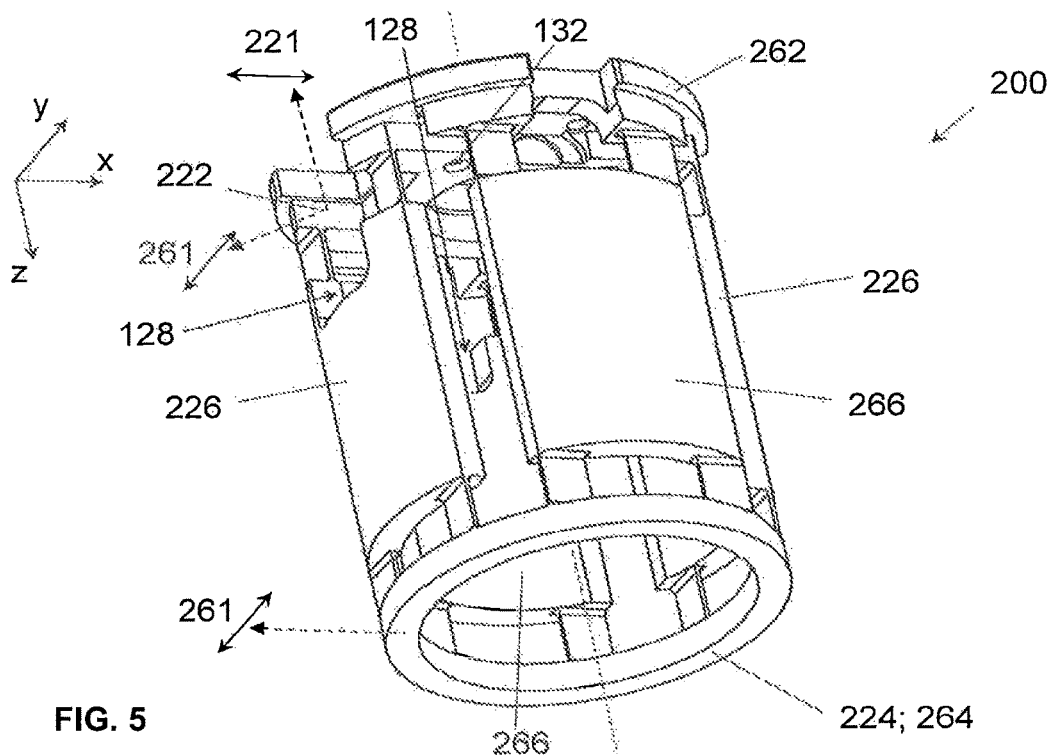
FIG. 5 shows a first isometric view of the parallel displacement mechanism.
Figure 6:
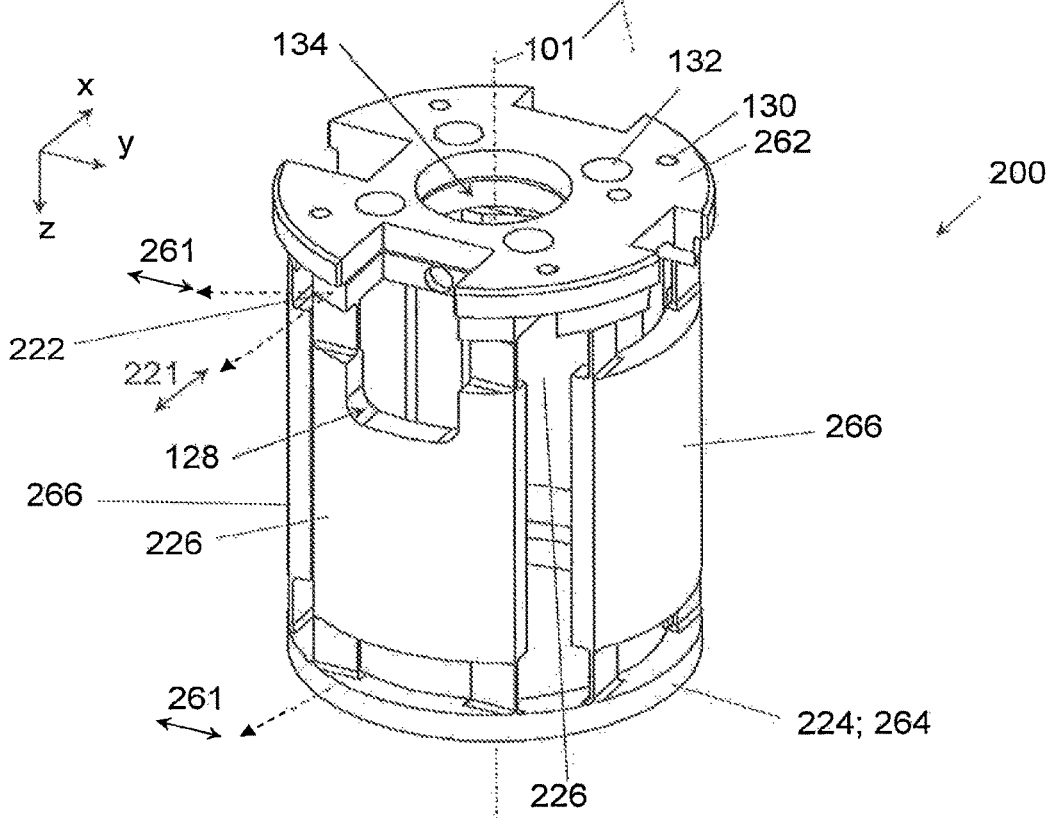
FIG. 6 shows a second isometric view of the parallel displacement mechanism.

FIGS. 5 and 6 show isometric views of the parallel displacement mechanism 200. The coaxial structure of the parallel displacement mechanism 200 around the lens axis is highly visible. Furthermore, an opening 134 can be seen which penetrates the parallel displacement mechanism 200 and the entire device 98. The opening 134 serves to retain the goniometer mechanism 300. Furthermore, threaded holes 130 can be seen in the first counter-element 262 (FIG. 6), which serve to affix the parallel displacement mechanism 200 and thus the device 98 in the second housing part 119. The through-holes 132 in the first counter-element 222 (FIG. 5) serve to connect the parallel displacement mechanism 200 with the goniometer mechanism 300. By means of the through-holes 132 in the first counter-element 262 (FIG. 6), screws can be guided through the first counter-element 262 and their screw heads can be inserted into the first counter-element 222. The parallel displacement mechanism is, like the goniometer mechanism 300 explained below, designed as a single part.

Figure 7:
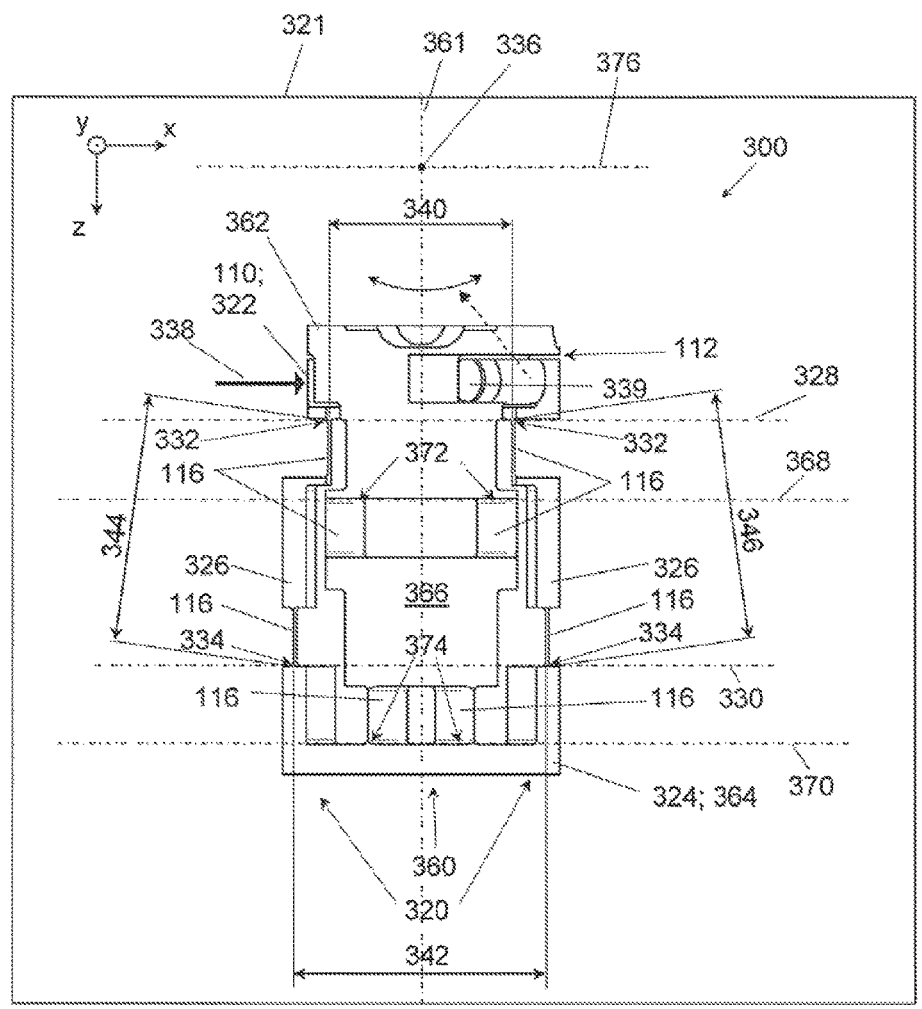
FIG. 7 shows a front view of a goniometer mechanism, wherein the arrangement of the pivoting means in the approximate form of an isosceles trapezoid is shown in dotted lines.
Figure 8:
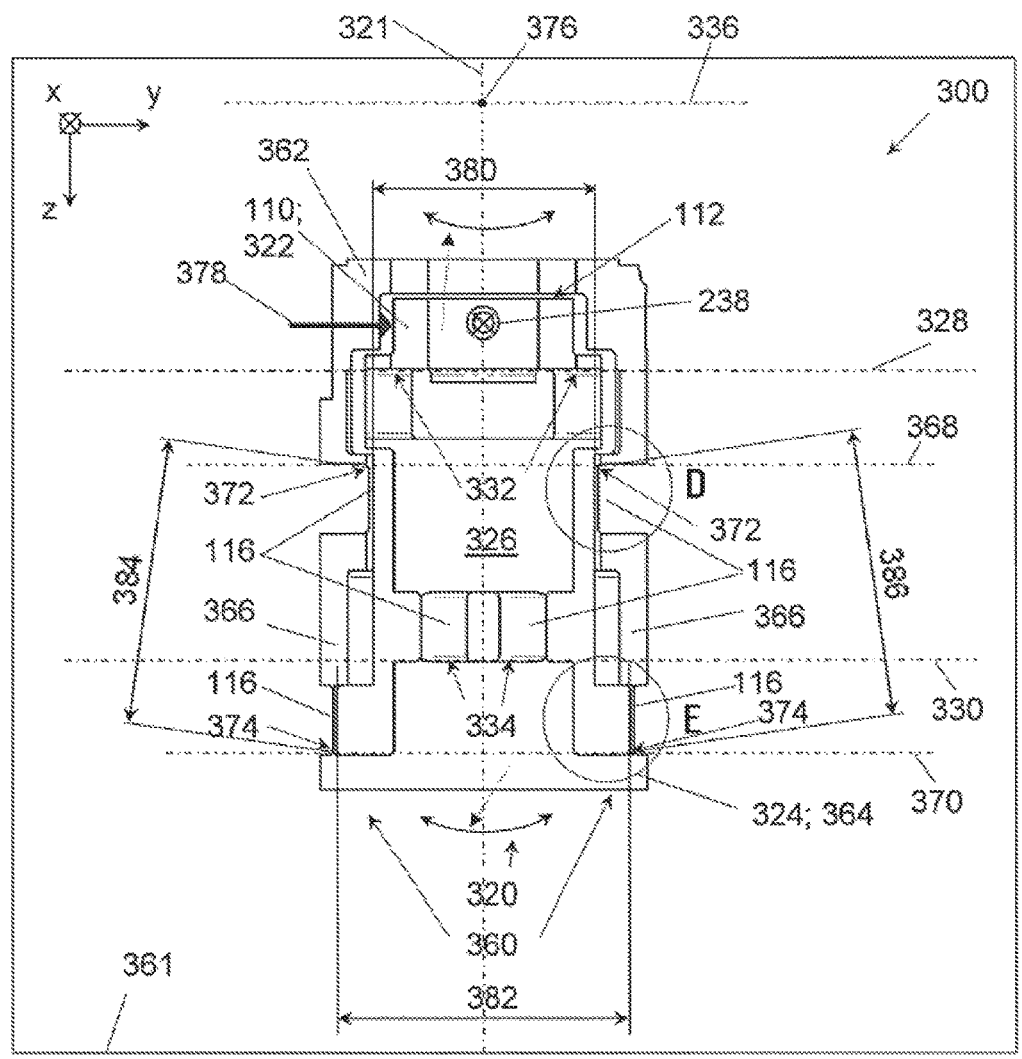
FIG. 8 shows a side view of the goniometer mechanism, wherein the arrangement of the pivoting means in the approximate form of an isosceles trapezoid is shown in dotted lines.

FIG. 7 shows a front view of the goniometer mechanism 300, with the direction of view counter to the y axis in the negative y direction. In this view, the first counter-element 322 of the first symmetrical, trapezoidal guide 320 is partially covered by the first counter-element 362 of the second symmetrical, trapezoidal guide 360, so that the gap 112 (see in particular FIG. 8) between the first counter-elements 322, 362 is only partially visible. FIG. 8 shows a side view of the goniometer mechanism 300 with the view in the direction of the x axis, i.e. in the positive x direction.

The flexure guides 116 connect the connecting elements 326, 366 with the counter-elements 322, 362, 324, 364, wherein the connection is achieved via at least one end 332, 372 (in the example shown, via two ends 332, 372 respectively) and at least one second end 334, 374 (in the example shown, via two ends 334, 374 respectively) of the connecting elements 326, 366. The flexure bearings 116 are dimensioned in such a manner with regard to their flexure rigidity and flexure values that a force applied to create flexure around the first pivot axis 336 (i.e. flexure in the x direction) or around the second pivot axis 376 (i.e. flexure in the y direction) is considerably lower compared to other spatial directions.

In the first trapezoidal guide 320, the connecting elements 326 are connected to the first counter-element 322 on a first connecting plane 328, which runs parallel to the first pivot axis 336, via two first ends 232 in each case. On a second connecting plane 330 which also runs parallel to the first pivot axis 336 and to the first connecting plane 330, the connecting elements 326 are in each case connected to the second counter-element 324 via two second ends 334. In the example shown, the second connecting plane 330 is an xy plane. Furthermore, the initial position shown, the first connecting plane 328 is parallel to the second connecting plane 330. The second counter-element 324 and the second connecting element 330 are offset from the first counter-element 322 and the first connecting plane 328 in the positive z direction.

Running in one direction along the first connecting plane 328 and at right-angles to the first pivot axis 336 (in the example in the x direction), the two first ends 332 of one of the connecting elements 326 comprise a first distance 340 in relation to the two first ends 332 of the other connecting element 326. Running in one direction along the second connecting plane 330 and at right-angles to the first pivot axis 336 (in the example in the x direction), the two second ends 334 of one of the connecting elements 326 also comprise a second distance 342 in relation to the two second ends 334 of the other connecting element 326. The first distance 340 is less than the second distance 342.

In directions along the progression of a plane 321 which runs at right-angles to the first pivot axis 336, the respective distances 344, 346 between the respective first ends 332 and the respective second ends 334 of the connecting elements 326 are equal. The two first ends 332 and the two second ends 334 of the respective connecting element 326 are offset in the direction of the first pivot axis 336, i.e. in the example, they are offset from each other in the y direction.

In order to conduct a goniometer movement of the lens 100 around the first pivot axis 336, a third adjusting force 338 is introduced to the first counter-element 322 by means of an adjusting element 114, wherein the third adjusting force 338 comprises a component at right-angles to the first pivot axis 336 and parallel to the first connecting plane 328. The third adjusting force 338 shown comprises a (sole) component in the positive x direction in the exemplary embodiment. Due to the third adjusting force 338, a flexure of the flexure bearings 116 and thus of necessity a goniometer movement of the first counter-element 322 is thus achieved, whereby the first counter-element 322 pivots at least approximately around the first pivot axis 336. As long as the second trapezoidal guide 360 is not actuated, the lens 100 is thus pivoted at least approximately on the plane 321.

The goniometer movement comes to an end when the forces are balanced. This results on the one hand from the third adjusting force 338, which acts in the positive x direction, and on the other hand from forces resulting from the flexure of the flexure bearings 116 as well as a spring force (not shown) which is brought about by a spring element 115 and which acts on a combined counter-bearing 339, among other things in the negative x direction. The spring element, which acts on the combined counter-bearing 339, brings a spring force to bear on the first counter-element 322 due to the inclined position within the xy plane, which counteracts both the third adjusting force 338 as well as the fourth adjusting force 378 (see FIG. 8). Due to a pre-tensioning of the spring element 115, a goniometer movement can also be conducted in the opposite pivot direction around the first pivot axis 336.

In the second trapezoidal guide 360, the connecting elements 368 are connected to the first counter-element 362 on a first connecting plane 328, which runs parallel to the second pivot axis 376, via two first ends 272 in each case. In the example shown, the first connecting plane 368 is an xy plane. On a second connecting plane 370 which also runs parallel to the second pivot axis 376 and to the first connecting plane 368, the connecting elements 366 are in each case connected to the second counter-element 364 via two second ends 374. In the initial position shown, the second connecting plane 370 is parallel to the first connecting plane 368. The second counter-element 364 and the second connecting element 370 are offset from the first counter-element 362 and the first connecting plane 368 in the positive z direction.

Running in one direction along the first connecting plane 368 and at right-angles to the second pivot axis 376 (in the example in the y direction), the two first ends 372 of one of the connecting elements 366 comprise a first distance 380 in relation to the two first ends 372 of the other connecting element 366. Running in one direction along the second connecting plane 370 and at right-angles to the second pivot axis 376 (in the example in the y direction), the two second ends 374 of one of the connecting elements 366 comprise a second distance 382 in relation to the two second ends 374 of the other connecting element 366. The first distance 380 is less than the second distance 382.

In directions along the progression of a plane 361 which runs at right-angles to the second pivot axis 376, the respective distances 384, 386 between the respective first ends 372 and the respective second ends 374 of the connecting elements 366 are equal. The two first ends 372 and the two second ends 374 of the respective connecting element 366 are offset in the direction of the second pivot axis 376, i.e. in the example, they are offset from each other in the x direction.

In order to conduct a goniometer movement of the lens 100 around the second pivot axis 376, a fourth adjusting force 378 is introduced to the first counter-element 322 by means of an adjusting element 114, wherein the fourth adjusting force 378 comprises a component at right-angles to the second pivot axis 376 and parallel to the second connecting plane 370. The fourth adjusting force 378 shown comprises a (sole) component in the positive y direction in the exemplary embodiment. The fourth adjusting force 378 is guided via the flexure bearings 116 of the first trapezoidal guide 320 which are rigid in the direction at right-angles to the second pivot axis 376 and parallel to the second connecting elements 370 to the joint second counter-element 324, 364 of the first and second trapezoidal guides 320, 360. Due to the fourth adjusting force 378, a flexure of the flexure bearings 116 of the second trapezoidal guide 360 and thus of necessity a goniometer movement of the second counter-element 324, 364 and of the first counter-element 322 is thus at least approximately achieved around the second pivot axis 376. As long as the first trapezoidal guide 320 is not actuated, the lens 100 is thus pivoted at least approximately on the plane 361.

The goniometer movement comes to an end when the forces are balanced. This results on the one hand from the fourth adjusting force 378, which acts in the positive y direction, and on the other hand from forces resulting from the flexure of the flexure bearings 116 as well as a spring force (not shown) which is brought about by a spring element 115 and which acts on a combined counter-bearing 339, among other things in the negative y direction. The spring element 115, which acts on the combined counter-bearing 339, brings, as already explained above, a spring force to bear on the first counter-element 322 due to the inclined position within the xy plane, which counteracts both the third adjusting force 338 as well as the fourth adjusting force 378. Due to a pre-tensioning of the spring element 115, a goniometer movement can also be conducted in the opposite pivot direction around the second pivot axis 376.

In the exemplary embodiment, the first connecting planes 328 and 368, as well as the second connecting planes 330, 370 of the trapezoidal guides 320, 360 are parallel to each other in the initial position shown.

In the details D and E, the flexure bearings 116 are shown in detail. In some cases, these comprise rounded transitions to the counter-elements 322, 324, 362, 364 and to the connecting elements 326, 366—symbolically shown as broken lines.

Figure 9:
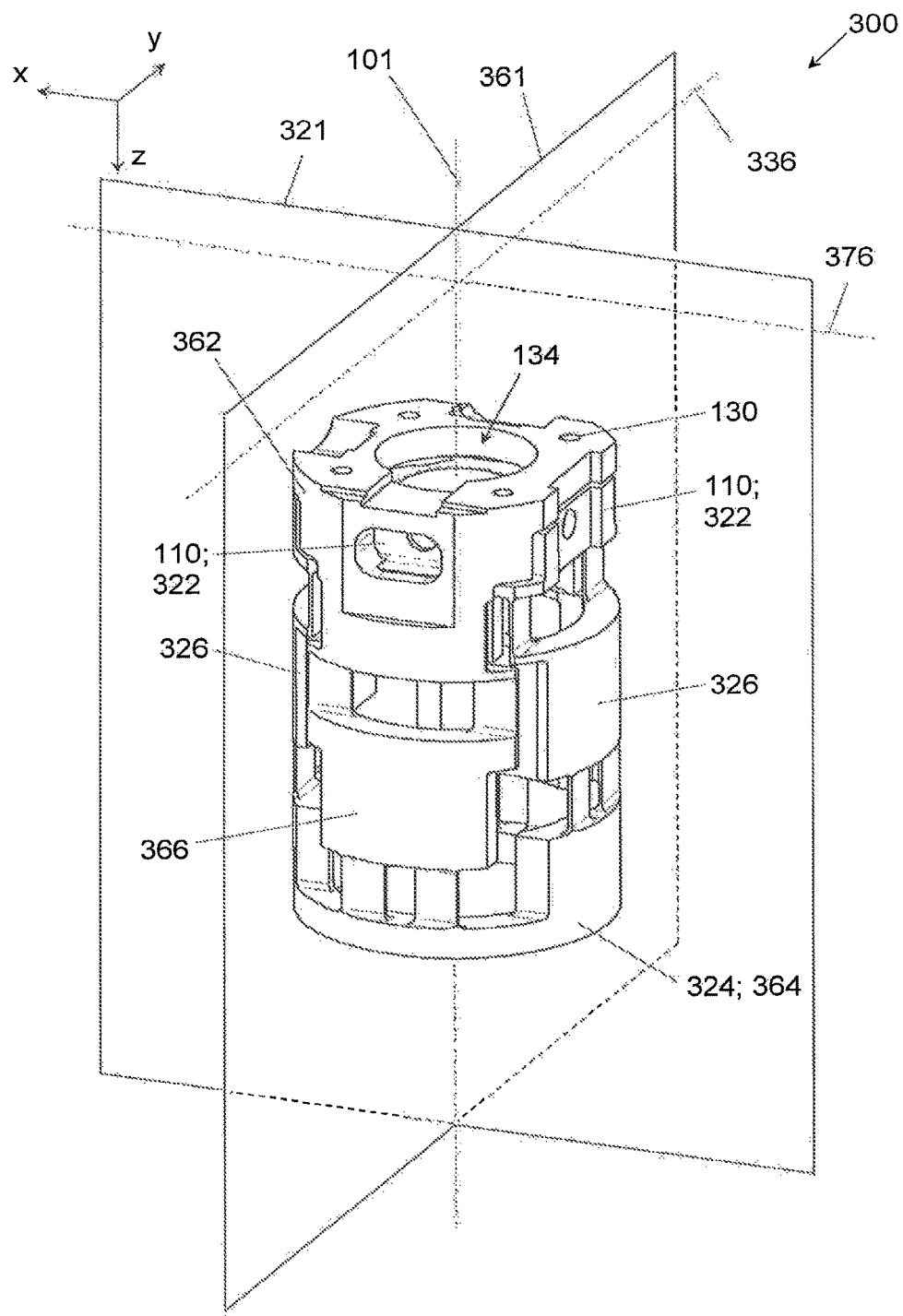
FIG. 9 shows a first isometric view of the goniometer mechanism.
Figure 10:
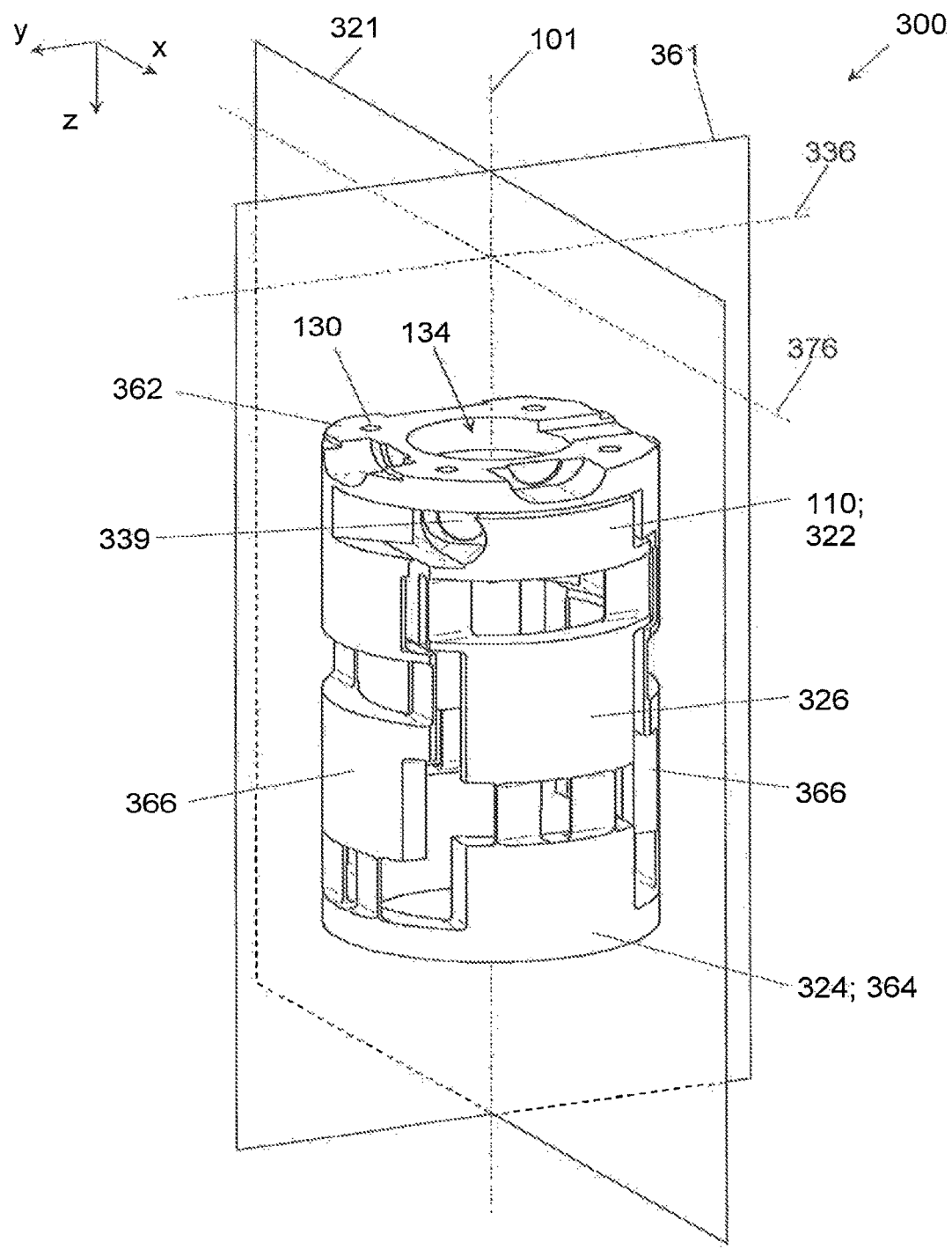
FIG. 10 shows a second isometric view of the goniometer mechanism.

FIGS. 9 and 10 show isometric views of the goniometer mechanism 300. The coaxial structure of the goniometer mechanism 300 around the lens axis is highly visible. Furthermore, an opening 134 can be seen which penetrates the goniometer mechanism 300 and the entire device 98. X-rays can penetrate through the device 98 through the opening 134. Furthermore, threaded holes 130 can be seen in the first counter-element 362, which serve to connect the goniometer mechanism 300 with the parallel displacement mechanism 200.

As can be seen in particular in FIGS. 1, 2, 5, 6, 9 and 10, the parallel displacement mechanism 200 and the goniometer mechanism 300 are essentially designed as a hollow cylinder, and are arranged coaxially to each other, wherein the goniometer mechanism 300 is arranged coaxially in the parallel displacement mechanism 200.

Thus, within the apparatus 96 (ref. FIGS. 1 and 2):
the lens 100 is connected to the retaining element 110 (or is screwed into the retaining element 110) and the retaining element 110 is designed as a single part with the first counter-element 322 of the first trapezoidal guide 320;
the first counter-element 322 is connected by means of the connecting elements 326 of the first trapezoidal guide 320 and its flexure bearings 116 to the second counter-element 324, 364, which is designed as a single part, of the first and second trapezoidal guides 320, 360;
the second counter-element 324, 364 is connected by means of the connecting elements 366 of the second trapezoidal guide 360 and its flexure bearings 116 to the first counter-element 362 of the second trapezoidal guide 360;
the first counter-element 362 of the second trapezoidal guide 360 is connected (or screwed) to the first counter-element 222 of the first parallel guide 220;
the first counter-element 222 is connected by means of the connecting elements 226 of the first parallelogram guide 220 and its flexure bearings 116 to the second counter-element 224, 264, which is designed as a single part, of the first and second parallelogram guides 220, 260;
the second counter-element 224, 264 is connected by means of the connecting elements 266 of the second trapezoidal guide 260 and its flexure bearings 116 to the first counter-element 262 of the second trapezoidal guide 360; and
the first counter-element 262 of the second parallelogram guide 260 is connected (or screwed) to the second housing part 119 of the apparatus 96.

Thus, by means of the device 98, a device for 2-point gauging is realised which among other things is suitable due to its compactness, vacuum resilience and excellent accessibility, even in the narrowest space and with restrictions resulting from machine technology. This is achieved through the realisation of the gauging kinematics, in particular of a 2-axis goniometer, by means of flexure bearings 116.

For gauging purposes, the entry focus 104 (with focal point on the entry side) of the lens 100 is gauged to the first predetermined point 102 (anode focal spot) with the aid of the two parallelogram guides 220, 260 (parallel axes). Then, the lens 100 is pivoted around the first predetermined point 102 until the exit focus 108 is gauged to the second predetermined point 106 (a target point on the sample surface). Thus, the device 98 decouples both partial gauging operations (anode side/sample side), as a result of which a simplified gauging procedure is realised.

Due to the coaxial structure, maximum installation space usage is achieved, as a result of which integration of the device is simplified.

The device 98 is characterised by a very low number of parts, since the two kinematics (axes) in each case are realised from a monolithic block. The embodiment shown is also characterised by design and optimisation ready for production. Several excitation sources can be used in one device, as long as the excitation points of all excitation sources can be gauged to each other.

LIST OF REFERENCE NUMERALS

96 Apparatus
98 Device
100 X-ray optics/capillary lens
101 Lens axis
102 First predetermined point
104 Optical entry point/entry focus
106 Second predetermined point 108 Optical exit point/exit focus
110 Retaining element
112 Gap
114 Adjusting elements
115 Spring element
116 Flexure bearing
118 First housing part
119 Second housing part
120 Holder
122 Window
124 Position of a spacer disc
126 Screw connection
128 Recess
130 Threaded hole
132 Through-hole
134 Opening
200 Parallel displacement mechanism
220 First parallel kinematics/first parallelogram guide
221 First parallel displacement direction
222 First counter-element
224 Second counter-element
226 Connecting element
228 First connecting plane
230 Second connecting plane
232 First end
234 Second end
238 First adjusting force
239 First counter-bearing
240 First distance
242 Second distance
244 Distance between first and second end of a first connecting element
246 Distance between first and second end of a second connecting element
260 Second parallel kinematics/second parallelogram guide
261 Second parallel displacement direction
262 First counter-element
264 Second counter-element
266 Connecting element
268 First connecting plane
270 Second connecting plane
272 First end
274 Second end
278 Second adjusting force
279 Second counter-bearing
280 First distance
282 Second distance
284 Distance between first and second end of a first connecting element
286 Distance between first and second end of a second connecting element
300 Goniometer mechanism
320 First goniometer kinematics/first trapezoidal guide
321 Plane at right-angles to the first pivot axis
322 First counter-element
324 Second counter-element
326 Connecting element
328 First connecting plane
330 Second connecting plane
332 First end
334 Second end
336 First pivot axis
338 Third adjusting force
339 Combined counter-bearing
340 First distance
342 Second distance
344 Distance between first and second end of a first connecting element
346 Distance between first and second end of a first connecting element
360 Second goniometer kinematics/second trapezoidal guide
361 Plane which extends at right-angles to the second pivot axis
362 First counter-element
364 Second counter-element
366 Connecting element
368 First connecting plane
370 Second connecting plane
372 First end
374 Second end
376 Second pivot axis
378 Fourth adjusting force
380 First distance
382 Second distance
384 Distance between first and second end of a first connecting element
386 Distance between first and second end of a second connecting element

The invention claimed is:

1. A device (98) for the spatial alignment of X-ray optics (100) with an optical entry point (104) and an optical exit point (108), comprising:
a retaining element (110) for retaining and affixing the X-ray optics (100), so that these are aligned in a z direction in an initial position, and the entry point (104) is essentially located on at least one pivot axis (336, 376) which is structurally predetermined by the device;
a parallel displacement mechanism (200) connected to the retaining element (110) for gauging the entry point (104) of the X-ray optics (100) to a first predetermined point (102), comprising:
first parallel kinematics (220) designed for the parallel displacement of the X-ray optics (100) essentially in a first parallel displacement direction (221) which differs from the z direction,
second parallel kinematics (260) designed for the parallel displacement of the X-ray optics (100) essentially in a second parallel displacement direction (261) which differs from the z direction and the first parallel displacement direction (221);
a goniometer mechanism (300) which is connected to the retaining element (110) and the parallel displacement mechanism (200) for gauging the exit point (108) of the X-ray optics (100) to a second predetermined point (106), wherein the goniometer mechanism (300) is designed to conduct at least approximately a pivoting movement of the X-ray optics (100) around the entry point (104), comprising:
first goniometer kinematics (320) designed to pivot the X-ray optics (100) at least approximately around a first pivot axis (336), wherein the first pivot axis (336) extends in a direction which differs from the z direction
wherein the parallel displacement mechanism (200) and the goniometer mechanism (300) are coaxially arranged within each other.

2. The device according to claim 1, wherein the first parallel kinematics (220) of the parallel displacement mechanism (200) are a first parallelogram guide (220) and/or the second parallel kinematics (260) of the parallel displacement mechanism (200) are a second parallelogram guide (260).

3. The device according to claim 1, wherein the goniometer mechanism (300) comprises second goniometer kinematics (360) designed to pivot the X-ray optics (100) at least approximately around a second pivot axis (376), wherein the second pivot axis (376) extends in a direction which differs from the z direction and the first pivot axis (336).

4. The device according to claim 3, wherein the first goniometer kinematics (320) are constructed as a first isosceles trapezoidal guide (320) and/or the second goniometer kinematics (360) are constructed as a second isosceles trapezoidal guide (360).

5. The device according to claim 4, wherein at least two of the guides (220, 260, 320, 360) comprise at least one first counter-element (222, 262, 322, 362) and one second counter-element (224, 264, 324, 364), which are connected to each other via a connection element pair (226, 266, 326, 366) of the respective guide (220, 260, 320, 360).

6. The device according to claim 5, wherein the first counter-elements (222, 262, 322, 362) are arranged between the second counter-element (224, 264, 324, 364) of the respective guide (220, 260, 320, 360) and the first pivot axis (336).

7. The device according to claim 5, wherein two of the first counter-elements (222, 262, 322, 362) or two of the second counter-elements (224, 264, 324, 364) of the at least two guides (220, 260, 320, 360) are immovably connected to each other or designed as a single part.

8. The device according to claim 5, wherein along a mechanical connection sequence, starting from the retaining element (110) through to a first (222, 262, 322, 362) or second counter-element (224, 264, 324, 364) designed to affix the device, the retaining element (110) is immovably connected to or designed as a single part with a first (222, 262, 322, 362) or second counter-element (224, 264, 324, 364), and on this basis, in alternation, the first counter-elements (222, 262, 322, 362) which belong to the parallelogram guides (220, 260) and/or trapezoidal guides (320, 360) are immovably connected to each other or designed as a single part and/or the second counter-elements (224, 264, 324, 364) are immovably connected to each other or designed as a single part.

9. The device according to claim 5, wherein
the retaining element (110) is immovably connected to or designed as a single part with the first counter-element (322) of the first trapezoidal guide (320),
the second counter-element (324) of the first trapezoidal guide (320) is immovably connected to or designed as a single part with the second counter-element (364) of the second trapezoidal guide (360),
the first counter-element (362) of the second trapezoidal guide (360) is immovably connected to or designed as a single part with the first counter-element (222) of the first parallelogram guide (220),
the second counter-element (224) of the first parallelogram guide (220) is immovably connected to or designed as a single part with the second counter-element (264) of the second parallelogram guide (260), and
the first counter-element (262) of the second parallelogram guide (260) is provided to affix the device (98).

10. The device according to claim 5, wherein the connecting elements (226, 266, 326, 366) of the connecting element pairs (226, 266, 326, 366) are respectively connected via ends (232, 234, 272, 274, 332, 334, 372, 374) of the connecting elements (226, 266, 326, 366) to the first counter-elements (222, 262, 322, 362) and the second counter-elements (224, 264, 324, 364).

11. The device according to claim 10, wherein the ends (232, 234, 272, 274, 332, 334, 372, 374) of the connecting elements (226, 266, 326, 366) comprise joints or a flexure bearing (116).

12. The device according to claim 5, wherein the parallelogram guides (220, 260) and/or the trapezoidal guides (320, 360) are arranged in relation to each other in such a manner that the X-ray optics (100) can essentially be retained centrally between the two respective connecting elements (226, 266, 326, 366) of the connecting element pairs by the retaining element (110).

13. The device according to claim 1, wherein the goniometer mechanism (300) is arranged coaxially within the parallel displacement mechanism (200).

14. The device according to claim 1, wherein the parallel displacement mechanism (200) is designed as a single part and/or the goniometer mechanism (300) is designed as a single part.

15. Apparatus (96) comprising the device (98) according to claim 1, and X-ray optics (100), which are retained and affixed in the retaining element (110) in such a manner that the X-ray optics (100) are aligned in the z direction (530) in an initial position, and the optical entry point (104) is essentially located on at least one pivot axis (336, 376) which is structurally predetermined by the device.

16. The device according to claim 11, wherein the ends (232, 234, 272, 274, 332, 334, 372, 374) of the connecting elements (226, 266, 326, 366) comprise one joint or one flexure bearing (116) at each end (232, 234, 272, 274, 332, 334, 372, 374).

* * * * *